US010988735B2

(12) United States Patent
Mei et al.

(10) Patent No.: US 10,988,735 B2
(45) Date of Patent: Apr. 27, 2021

(54) CARDIAC TISSUES CONTAINING SEMICONDUCTOR NANOMATERIALS AND METHODS OF PREPARING AND USING THE SAME

(71) Applicants: Clemson University Research Foundation, Clemson, SC (US); MUSC Foundation for Research Development, Charleston, SC (US); The University of Chicago, Chicago, IL (US)

(72) Inventors: Ying Mei, Mount Pleasant, SC (US); Tan Yu, Charleston, SC (US); Dylan Richards, Charleston, SC (US); Donald R. Menick, Isle of Palms, SC (US); Bozhi Tian, Chicago, IL (US)

(73) Assignees: Clemson University Research Foundation, Clemson, SC (US); MUSC Foundation for Research Development, Charleston, SC (US); The University of Chicago, Chicago, IL (US)

(*) Notice: Subject to any disclaimer, the term of this patent is extended or adjusted under 35 U.S.C. 154(b) by 27 days.

(21) Appl. No.: 15/543,701

(22) PCT Filed: Jan. 15, 2016

(86) PCT No.: PCT/US2016/013647
§ 371 (c)(1),
(2) Date: Jul. 14, 2017

(87) PCT Pub. No.: WO2016/115489
PCT Pub. Date: Jul. 21, 2016

(65) Prior Publication Data
US 2017/0369847 A1    Dec. 28, 2017

Related U.S. Application Data

(60) Provisional application No. 62/104,258, filed on Jan. 16, 2015.

(51) Int. Cl.
| | | |
|---|---|---|
| C12N 5/077 | (2010.01) | |
| G01N 33/50 | (2006.01) | |
| A61K 35/34 | (2015.01) | |
| A61L 27/30 | (2006.01) | |
| A61L 27/38 | (2006.01) | |

(52) U.S. Cl.
CPC ............ *C12N 5/0657* (2013.01); *A61K 35/34* (2013.01); *A61L 27/306* (2013.01); *A61L 27/3804* (2013.01); *A61L 27/3826* (2013.01); *A61L 27/3886* (2013.01); *G01N 33/5061* (2013.01); *A61L 2400/12* (2013.01); *A61L 2430/20* (2013.01); *C12N 2503/02* (2013.01); *C12N 2506/45* (2013.01); *C12N 2513/00* (2013.01); *C12N 2533/10* (2013.01)

(58) Field of Classification Search
None
See application file for complete search history.

(56) References Cited

U.S. PATENT DOCUMENTS

| | | | |
|---|---|---|---|
| 5,266,480 A | 11/1993 | Naughton et al. | |
| 5,770,417 A | 6/1998 | Vacanti et al. | |
| 6,537,567 B1 | 3/2003 | Niklason et al. | |
| 6,962,814 B2 | 11/2005 | Mitchell et al. | |
| 2014/0073063 A1* | 3/2014 | Lieber ............... | H01L 51/0504 438/1 |

FOREIGN PATENT DOCUMENTS

WO    WO 2014/144219 A1    9/2014

OTHER PUBLICATIONS

Stevens, Kelly. et al. Scaffold-Free Human Cardiac Tissue Patch Created from Embryonic Stem Cells. Tissue Engineering: Part A. vol. 15, No. 6, 2009. (Year: 2009).*
Anderson et al. "Dissolution of different forms of partially porous silicon wafers under simulated physiological conditions" *Physica Status Solidi (a)* 197(2):331-335 (2003).
Beauchamp et al. "Electrical Propagation in Synthetic Ventricular Myocyte Strands From Germline Connexin43 Knockout Mice" *Circulation Research* 95:170-178 (2004).
Beauchamp et al. "Electrical Coupling and Propagation in Engineered Ventricular Myocardium With Heterogeneous Expression of Connexin43" *Circulation Research* 110:1445-1453 (2012).
Bub et al. "Measurement and analysis of sarcomere length in rat cardiomyocytes in situ and in vitro" *American Journal of Physiology: Heart and Circulatory Physiology* 298:H1616-H1625 (2010).
Casey et al. "Hibernation in Noncontracting Mammalian Cardiomyocytes" *Circulation* 102:3124-3129 (2000).
Chong et al. "Human Embryonic Stem Cell-Derived Cardiomyocytes Regenerate Non-Human Primate Hearts" *Nature* 510(7504):273-277 (2014).
Desroches et al. "Functional scaffold-free 3-D cardiac microtissues: a novel model for the investigation of heart cells" *American Journal of Physiology: Heart and Circulatory Physiology* 302:H2031-H2042 (2012).
Duan et al. "Nanoelectronics-biology frontier: From nanoscopic probes for action potential recording in live cells to three-dimensional cyborg tissues" *Nano Today* 8(4):351-373 (2013).
Dvir et al. "Nanowired three dimensional cardiac patches" *Nature Nanotechnology* 6(11):720-725 (2011).

(Continued)

*Primary Examiner* — Nghi V Nguyen
(74) *Attorney, Agent, or Firm* — Myers Bigel, P.A.

(57) ABSTRACT

Described herein are tissues containing semiconductor nanomaterials. In some embodiments, the tissues include vascular cells, cardiomyocytes, and/or cardiac fibroblasts. The tissue may be scaffold-free. In some embodiments, the tissue includes an electrically conductive network. The tissue may exhibit synchronized electrical signal propagation within the tissue. In some embodiments, the tissue exhibits increased functional assembly of cardiac cells and/or increased cardiac specific functions compared to a cardiac tissue prepared using a conventional tissue culture method. Methods of preparing and using such tissues are also described herein.

19 Claims, 14 Drawing Sheets

(56) References Cited

OTHER PUBLICATIONS

Fine et al. "Human-induced pluripotent stem cell-derived cardiomyocytes for studies of cardiac ion transporters" *American Journal of Physiology: Cell Physiology* 305:C481-C491 (2013).
Garipcan et al. "In Vitro Biocompatibility of n-Type and Undoped Silicon Nanowires" *Advanced Engineering Materials* 13(1-2):B3-B9 (2011).
Jiang et al. "Medicinal Surface Modification of Silicon Nanowires: Impact on Calcification and Stromal Cell Proliferation" *Applied Materials & Interfaces* 1(2):266-269 (2009).
Kelm et al. "Design of Artificial Myocardial Microtissues" *Tissue Engineering* 10(1/2):201-214 (2004).
Kensah et al. "Murine and human pluripotent stem cell-derived cardiac bodies form contractile myocardial tissue in vitro" *European Heart Journal* 34:1134-1146 (2013).
Laflamme et al. "Cardiomyocytes derived from human embryonic stem cells in pro-survival factors enhance function of infarcted rat hearts" *Nature Biotechnology* 25(9):1015-1024 (2007).
Lieu et al. "Mechanism-Based Facilitated Maturation of Human Pluripotent Stem Cell-Derived Cardiomyocytes" *Circulation: Arrhythmia and Electrophysiology* 6:191-201 (2013).
Lundy et al. "Structural and Functional Maturation of Cardiomyocytes Derived from Human Pluripotent Stem Cells" *Stem Cells and Development* 22(14):1-12 (2013).
Martinelli et al. "Carbon Nanotubes Instruct Physiological Growth and Functionally Mature Syncytia: Nongenetic Engineering of Cardiac Myocytes" *ACS Nano* 7(7):5746-5756 (2013).
Mazzoleni et al. "Conductivity Values of Tissue Culture Medium From 20° C. to 40° C." *Bioelectromagnetics* 7:95-99 (1986).
Mignone et al. "Cardiogenesis From Human Embryonic Stem Cells" *Circulation Journal* 74:2517-2526 (2010).
Mihic et al. "The effect of cyclic stretch on maturation and 3D tissue formation of human embryonic stem cell-derived cardiomyocytes" *Biomaterials* 35:2798-2808 (2014).
Nagesha et al. "Biorelevant Calcification and Non-Cytotoxic Behavior in Silicon Nanowires" *Advanced Materials* 17(7):921-924 (2005).
Nunes et al. "Biowire: a platform for maturation of human pluripotent stem cell-derived cardiomyocytes" *Nature Methods* 10(8):781-787 (2013).
Oberpenning et al. "De novo reconstruction of a functional mammalian urinary bladder by tissue engineering" *Nature Biotechnology* 17:149-155 (1999).
Radisic et al. "Functional assembly of engineered myocardium by electrical stimulation of cardiac myocytes cultured on scaffolds" *Proceedings of the National Academy of Sciences* 101(52):18129-18134 (2004).
Radisic et al. "Oxygen Gradients Correlate With Cell Density and Cell Viability in Engineered Cardiac Tissue" *Biotechnology and Bioengineering* 93(2):332-343 (2006).
Rana et al. "Characterization of Human-Induced Pluripotent Stem Cell-Derived Cardiomyocytes: Bioenergetics and Utilization in Safety Screening" *Toxicological Sciences* 130(1):117-131 (2012).
Rezakhaniha et al. "Experimental investigation of collagen waviness and orientation in the arterial adventitia using confocal laser scanning microscopy" *Biomechanics and Modeling in Mechanobiology* 11(3-4):461-473 (2012).
Rodriguez et al. "Substrate Stiffness Increases Twitch Power of Neonatal Cardiomyocytes in Correlation with Changes in Myofibril Structure and Intracellular Calcium" *Biophysical Journal* 101:2455-2464 (2011).
Roger et al. "Heart Disease and Stroke Statistics—2011 Update: A Report From the American Heart Association" *Circulation* 123:e18-e209 (2011).
Schmidt et al. "Silicon Nanowires: A Review on Aspects of their Growth and their Electrical Properties" *Advanced Materials* 21:2681-2702 (2009).
Shiba et al. "Human ES-cell-derived cardiomyocytes electrically couple and suppress arrhythmias in injured hearts" *Nature* 489:322-327 (2012).
Shin et al. "Carbon-Nanotube-Embedded Hydrogel Sheets for Engineering Cardiac Constructs and Bioactuators" *ACS Nano* 7(3):2369-2380 (2013).
Tan et al. "Silicon Nanowire-Induced Maturation of Cardiomyocytes Derived from Human Induced Pluripotent Stem Cells" *Nano Letters* 15:2765-2772 (2015).
Tian et al. "Synthetic Nanoelectronic Probes for Biological Cells and Tissue" *Annual Review of Analytical Chemistry* 6:31-51 (2013).
Tölli et al. "In vivo biocompatibility of porous silicon biomaterials for drug delivery to the heart" *Biomaterials* 35:8394-8405 (2014).
Van Den Heuvel et al. "Lessons from the heart: Mirroring electrophysiological characteristics during cardiac development to in vitro differentiation of stem cell derived cardiomyocytes" *Journal of Molecular and Cellular Cardiology* 67:12-25 (2014).
Wu et al. "Controlled Growth and Structures of Molecular-Scale Silicon Nanowires" *Nano Letters* 4(3):433-436 (2004).
Yang et al. "Engineering Adolescence: Maturation of Human Pluripotent Stem Cell-Derived Cardiomyocytes" *Circulation Research* 114:511-523 (2014).
You et al. "Nanoengineering the Heart: Conductive Scaffolds Enhance Connexin 43 Expression" *Nano Letters* 11:3643-3648 (2011).
Zhang et al. "Tissue-engineered cardiac patch for advanced functional maturation of human ESC-derived cardiomyocytes" *Biomaterials* 34:5813-5820 (2013).
Zheng et al. "Synthesis and Fabrication of High-Performance n-Type Silicon Nanowire Transistors" *Advanced Materials* 16(21):1890-1893 (2004).
Zhou et al. "Engineering the heart: Evaluation of conductive nanomaterials for improving implant integration and cardiac function" *Scientific Reports* 4(3733):1-11 (2014).
Zhou et al. "Long Term Stability of Nanowire Nanoelectronics in Physiological Environments" *Nano Letters* 14:1614-1619 (2014).
International Search Report and the Written Opinion of the International Searching Authority corresponding to International Patent Application No. PCT/US2016/013647 (9 pages) (dated Mar. 31, 2016).
Mi et al. "Micromolding of PDMS scaffolds and microwells for tissue culture and cell patterning: A new method of microfabrication by the self-assembled micropatterns of diblock copolymer micelles" *Polymer* 47:5124-5130 (2006).

* cited by examiner

CARDIAC TISSUES CONTAINING SEMICONDUCTOR NANOMATERIALS AND METHODS OF PREPARING AND USING THE SAME

RELATED APPLICATION DATA

This application claims the benefit of and priority to U.S. Provisional Patent Application Ser. No. 62/104,258, filed Jan. 16, 2015, the disclosure of which is incorporated herein by reference in its entirety.

STATEMENT OF GOVERNMENT SUPPORT

This invention was made with government support under Grant Nos. GM103444, GM103342, HL 085847, and HL007260 awarded by the National Institutes of Health and Grant No. EPS-0903795 awarded by the National Science Foundation. The government has certain rights in the invention.

FIELD

The present invention relates generally to tissues containing semiconductor nanomaterials and methods of preparing and using the same.

BACKGROUND

Cardiac tissue engineering may be desirable to provide functional heart tissue replacement for drug screening and heart repair. To this end, scaffold-based tissue engineering approaches have been extensively used to provide 3D microenvironments to promote cardiac tissue formation. However, current scaffolds lack the matched physical/chemical/biological properties of native extracellular environments of myocardium. On the other hand, scaffold-free, 3D cardiac spheroids (i.e., spherical-shaped microtissues) prepared by seeding cardiomyocytes into agarose microwells were shown to improve cardiac functions. However, cardiomyocytes within the spheroids could not assemble in a controlled manner and led to compromised, unsynchronized contractions.

There remains a need for improved tissues and methods for preparing such tissues that can be used for therapeutic and drug testing purposes.

SUMMARY

According to an aspect of the present invention, provided are tissues including muscle cells (e.g., cardiac cells, such as, for example, cardiomyocytes and/or cardiac fibroblasts) and a semiconductor nanomaterial. The tissue may be a microtissue. The tissue may further include vascular cells such as, for example, endothelial cells.

The semiconductor nanomaterial may be an n-type or a p-type semiconductor material. The semiconductor nanomaterial may have a diameter and/or width of about 10 nm to about 200 nm and/or may have a length of about 1 µm to about 20 µm. The semiconductor nanomaterial may comprise a silicon nanomaterial, such as, for example, a phosphorous-doped silicon and/or a boron-doped silicon nanomaterial.

According to yet another aspect of the present invention, provided are methods of preparing a muscle tissue including muscle cells and a semiconductor nanomaterial. The tissue may be a cardiac tissue including cardiac cells and a semiconductor nanomaterial. The tissue may further include vascular cells such as, for example, endothelial cells.

One aspect of the present invention includes a method of preparing a tissue (e.g., cardiac tissue), the method including seeding a substrate with a cell suspension comprising a plurality of cells (e.g., cardiac cells and/or vascular cells) and a semiconductor nanomaterial to form a cell culture, thereby preparing the tissue.

Another aspect of the present invention includes a method of treating a subject including introducing a tissue of the present invention into the subject and/or providing a tissue of the present invention to the subject.

A further aspect of the present invention includes a method of screening a compound (e.g., a chemical and/or biological compound) or composition, the method including introducing and/or contacting the compound or composition to a tissue of the present invention. The method may further include detecting a response to the compound or composition. A positive response may indicate that the compound or composition is active when introduced to and/or in contact with the tissue, and a negative response may indicate that the compound or composition is inactive when introduced to and/or in contact with the tissue.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Figure 4:
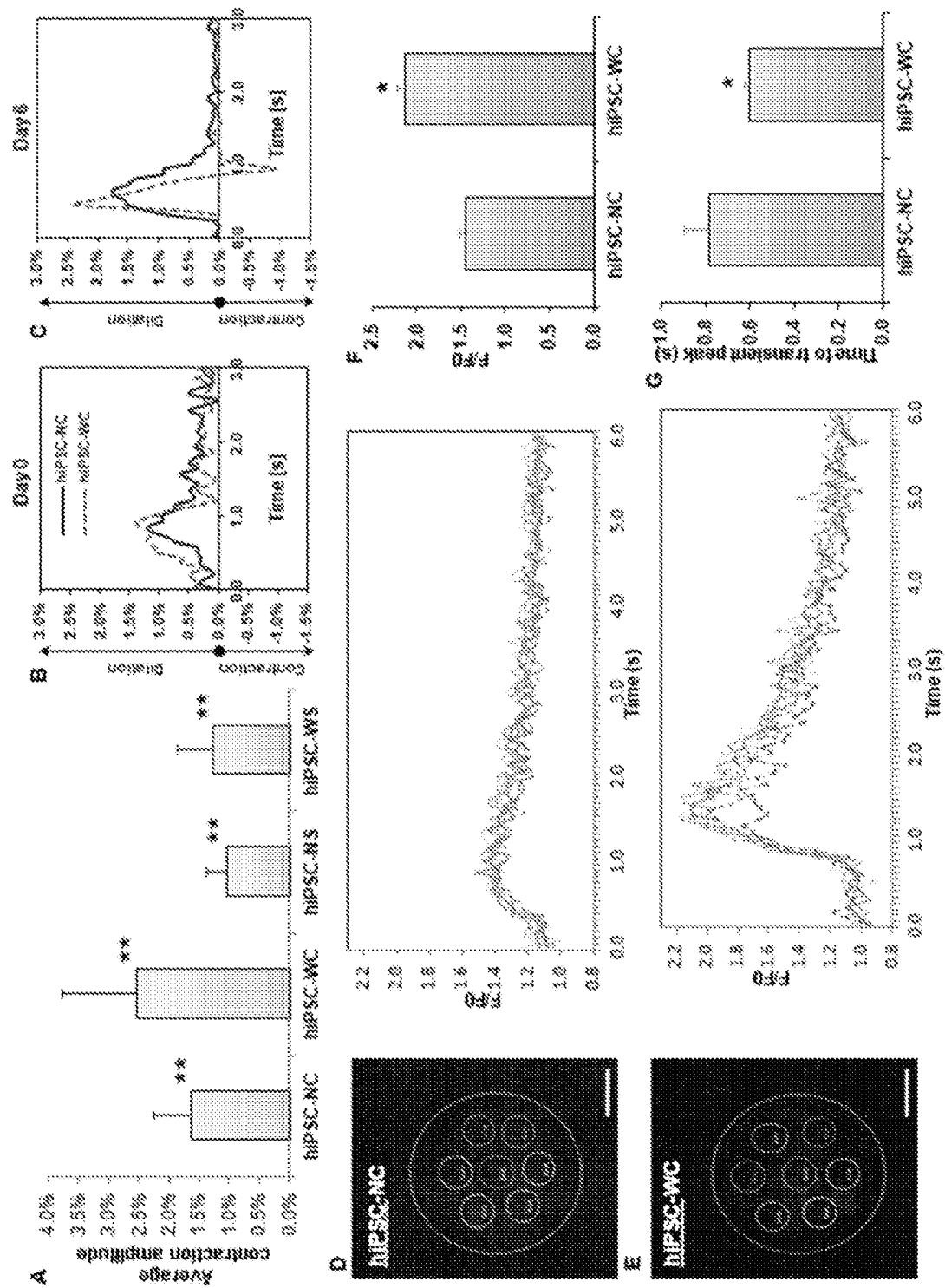

FIG. 4. Functional analysis of hiPSC-derived cardiomyocyte spheroids. (A) Average contraction amplitude from Day 1 to Day 7 of each group. Double asterisk (**) represents statistical difference between all groups. (B, C) Representative fractional area change (i.e., contraction amplitude) of spontaneously beating spheroids with and without e-SiNWs at time points Day 0 and Day 6, respectively; n=6 spheroids per condition. (D, E) Representative calcium transient imaging of seven regions of interest (smaller circles within larger circle) per spheroid for each group. Fluorescence amplitude, F/F0, refers to measured fluorescence intensity normalized to background fluorescence intensity. (F) Comparison of the peak value of F/F0 for each group. (n=3) (G) Comparison of calcium release duration for each group. (n=3) hiPSC-NC=human induced pluripotent stem cell cardiac spheroids, no e-SiNWs, no stimulation; hiPSC-WC=human induced pluripotent stem cell cardiac spheroids, with e-SiNWs, no stimulation. hiPSC-NS=human induced pluripotent stem cell cardiac spheroids, no e-SiNWs, with stimulation; hiPSC-WS=human induced pluripotent stem cell cardiac spheroids, with e-SiNWs, with stimulation. Asterisks (*) represent statistical significance with p<0.05; error bar represents standard deviation. Scale bars=100 µm.

Figure 5:
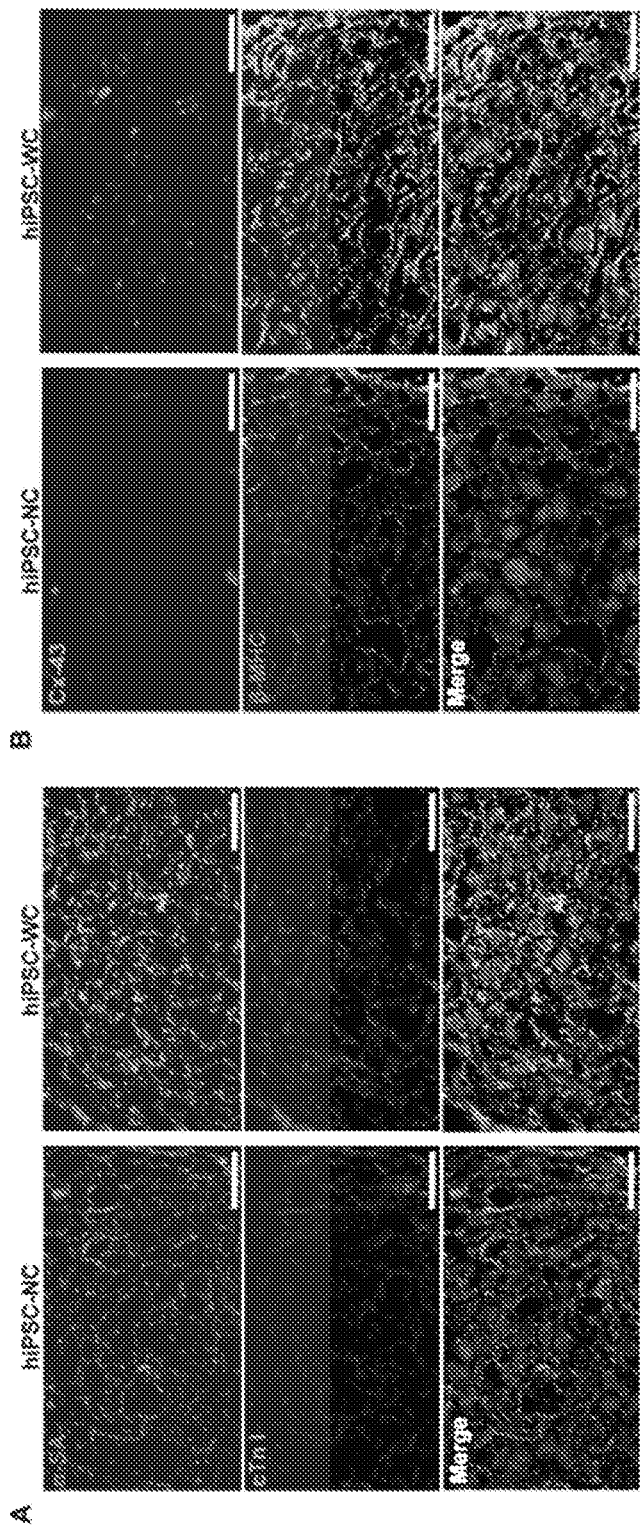
Figure 5:
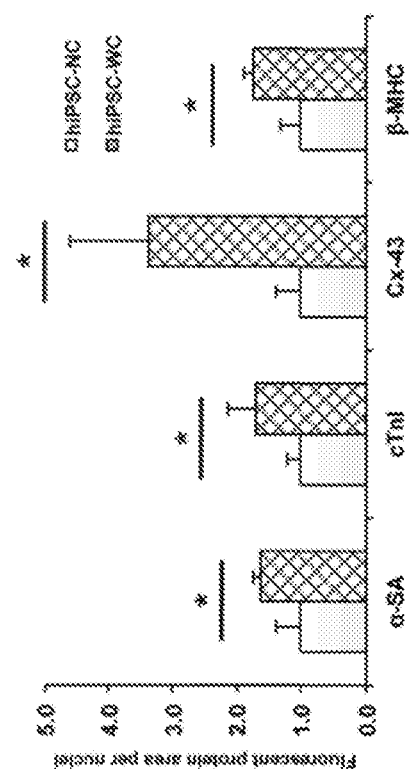

FIG. 5. Structural analysis of hiPSC-derived cardiomyocyte spheroids. (A) Immunofluorescent staining of alpha sarcomeric actinin (α-SA) and troponin I (cTn I). (B) Immunofluorescent staining of connexin-43 (Cx-43) and beta myosin heavy chain (φ-MHC). (C) Protein expression analysis based on fluorescent signal-covered area per nuclei normalized over hiPSCNC expression (n=3; 75 µm×130 µm picture regions, at least containing >50 nuclei) based on (A, B). hiPSC-NC=human induced pluripotent stem cell cardiac spheroids, no e-SiNWs, no stimulation; hiPSC-WC=human induced pluripotent stem cell cardiac spheroids, with e-SiNWs, no stimulation. Asterisks (*) represent statistical significance with p<0.05; error bar represents standard deviation. Scale bars=20 µm.

Figure 6:
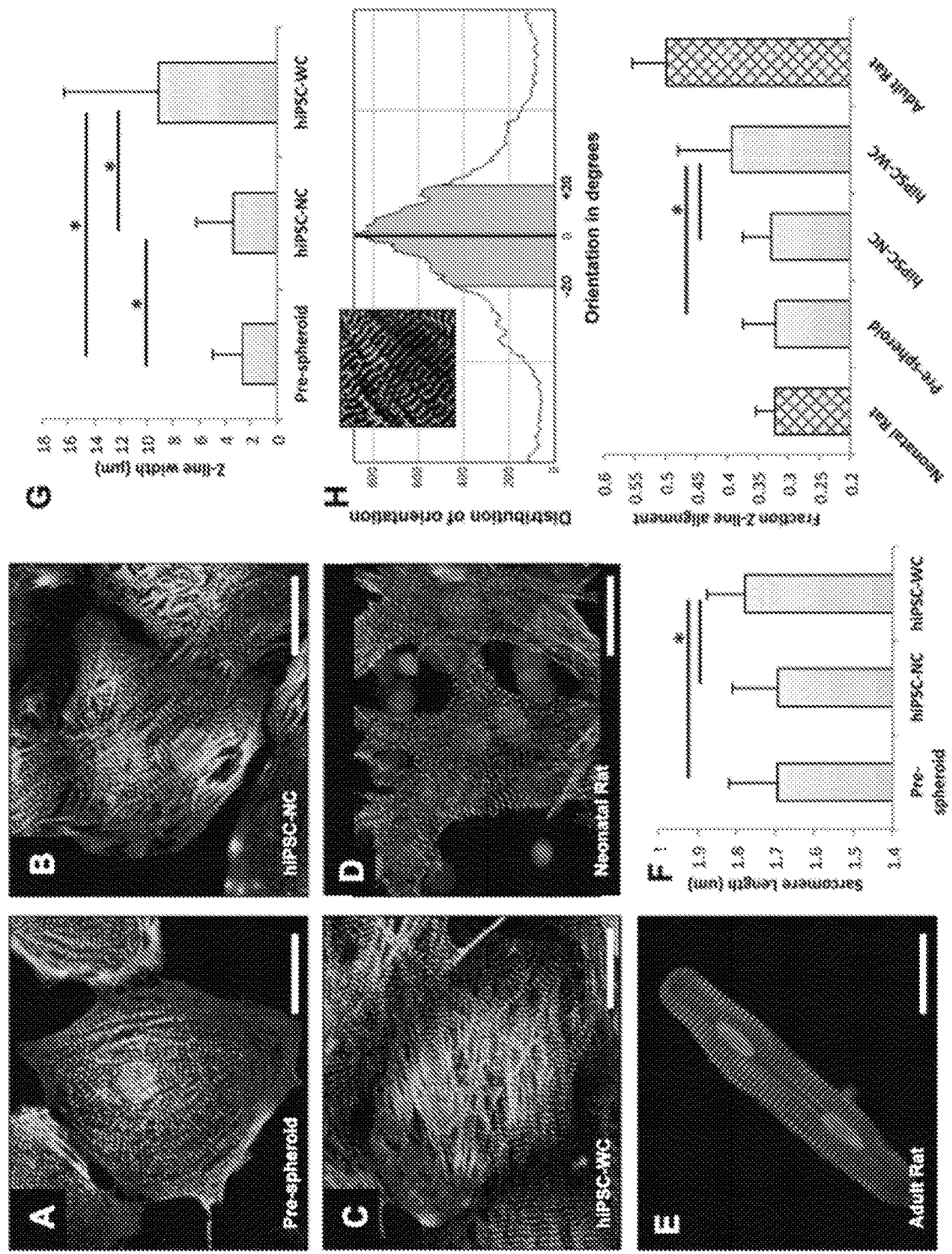

FIG. 6. Single cell analysis of hiPSC-derived cardiomyocytes before and after spheroids as well as rat-neonatal and adult cardiomyocytes. (A) Fluorescent confocal images (light grey, α-sarcomeric actinin (α-SA); medium grey, troponin I; medium grey, DAPI nuclear stain) of single cells harvested before hiPSC spheroid fabrication, (B) after 7 days from hiPSC-NC spheroids, (C) and after 7 days from hiPSC-WC spheroids. (D) Rat-neonatal cardiomyocyte and (E) adult left ventricular cardiomyocyte for morphological comparison. (F) Sarcomere length measured as distance between α-SA-stained Z-line structures from cardiomyocytes with visible sarcomere structures; n=9 cells per condition. (G) Z-line width measurements based on α-SA-stained Z-line structures in comparison to neonatal and adult rat cardiomyocyte references; n=10 cells per condition. (H) Z-line alignment calculations were based on a fraction (±20° of the peak orientation degree) of aligned α-SA-stained structures; n=12 cells (hiPSC), 4 cells (rat) per condition. hiPSC-NC=human induced pluripotent stem cell cardiac spheroids, no e-SiNWs, no stimulation; hiPSC-WC=human induced pluripotent stem cell cardiac spheroids, with e-SiNWs, no stimulation. Asterisks (*) represent statistical significance with p<0.05; error bars represent standard deviation. Scale bars=25 µm.

Figure 7:
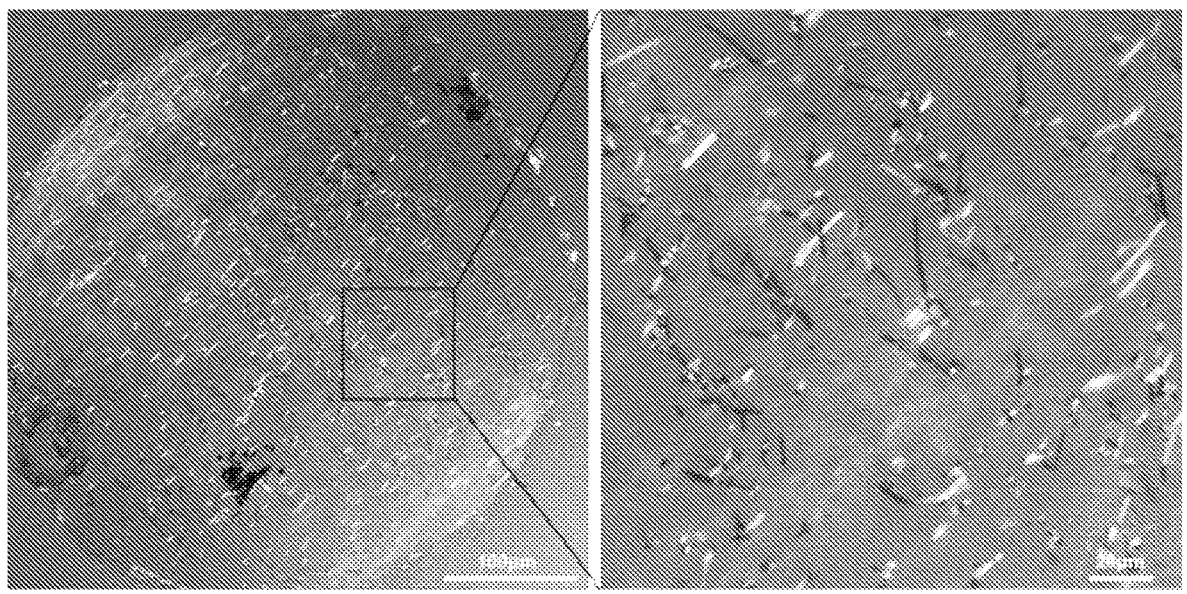

FIG. 7. DIC image of the e-SiNW-reinforced human cardiac spheroids shows the uniform distribution of e-SiNWs within the spheroids at a 1:1 ratio (number of cells/number of e-SiNWs).

Figure 8:
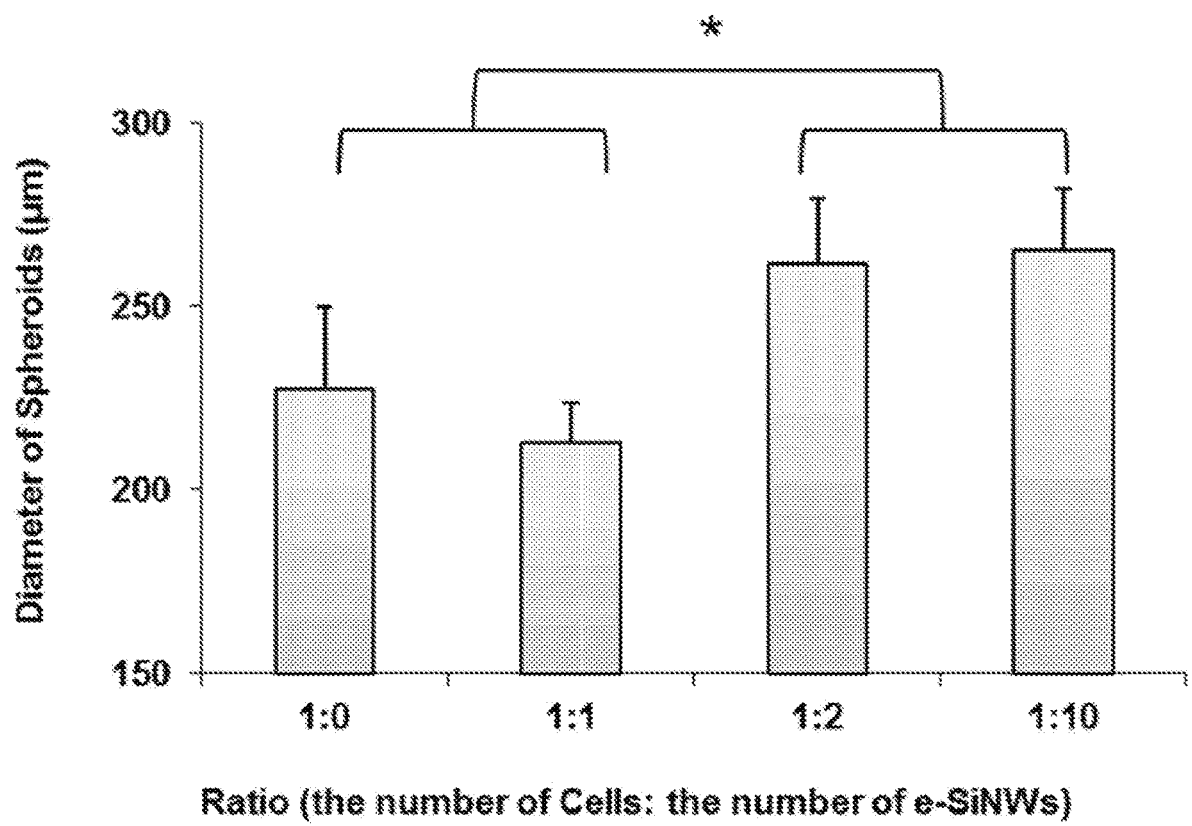

FIG. 8. Changes in diameter of rat-neonatal cardiac spheroids using different ratios of cells to e-SiNWs on Day 0; n=6 spheroids per condition. Asterisks (*) represent statistical significance with p<0.05; error bar represents standard deviation.

Figure 9:
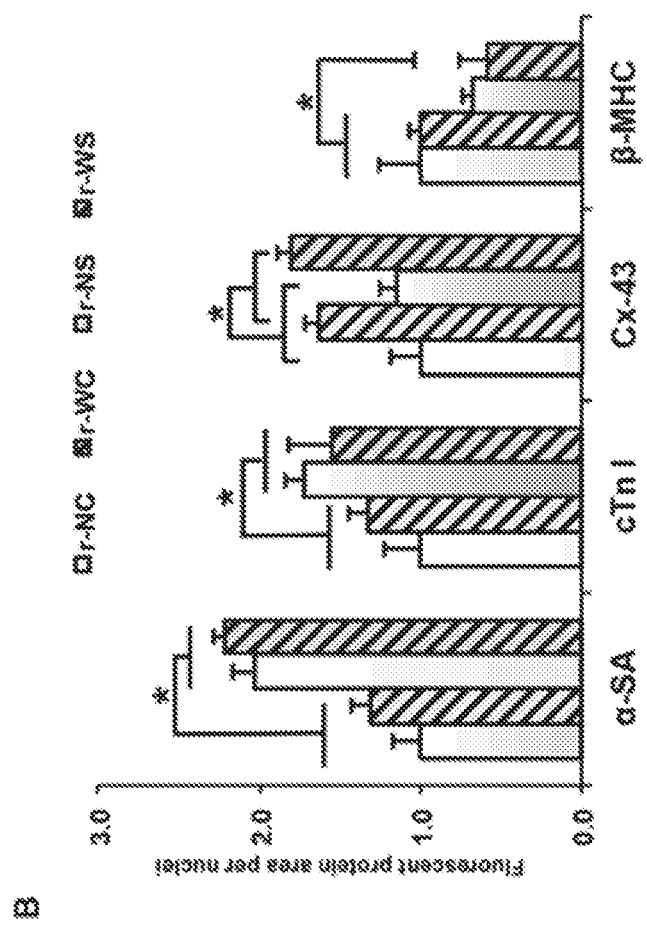
Figure 9:
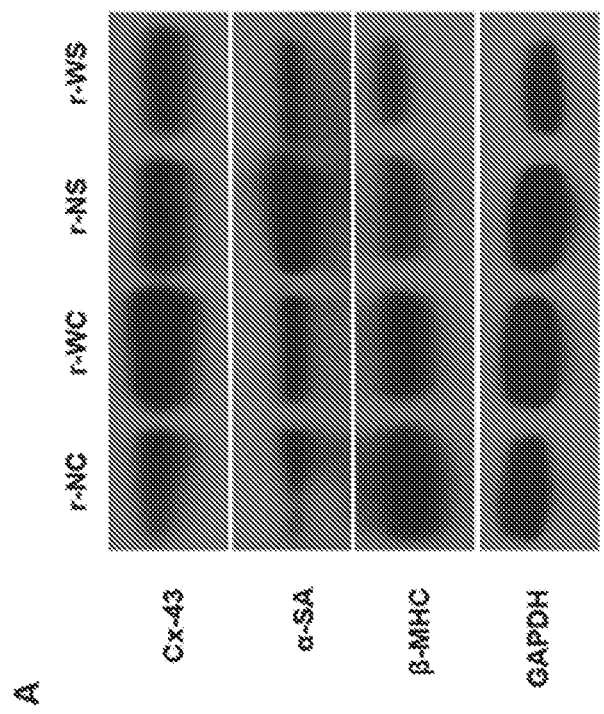

FIG. 9. Protein expression analysis of rat-neonatal cardiac spheroids after 7 days of treatment. (A) Western blot of cardiac-specific proteins after 7 days for all 4 groups. (B) Protein expression levels based on fluorescent signal-covered area per nuclei normalized over r-NC expression; n=3 picture regions; 50 µm×80 µm picture regions, at least containing >24 nuclei. r-NC=rat-neonatal cardiac spheroids, no e-SiNWs, no stimulation; r-NS=rat-neonatal cardiac spheroids, no e-SiNWs, with stimulation; r-WC=rat-neonatal cardiac spheroids, with e-SiNWs, no stimulation; r-WS=rat-neonatal cardiac spheroids, with e-SiNWs, with stimulation. Asterisks (*) represent statistical significance with p<0.05; error bar represents standard deviation.

Figure 10:
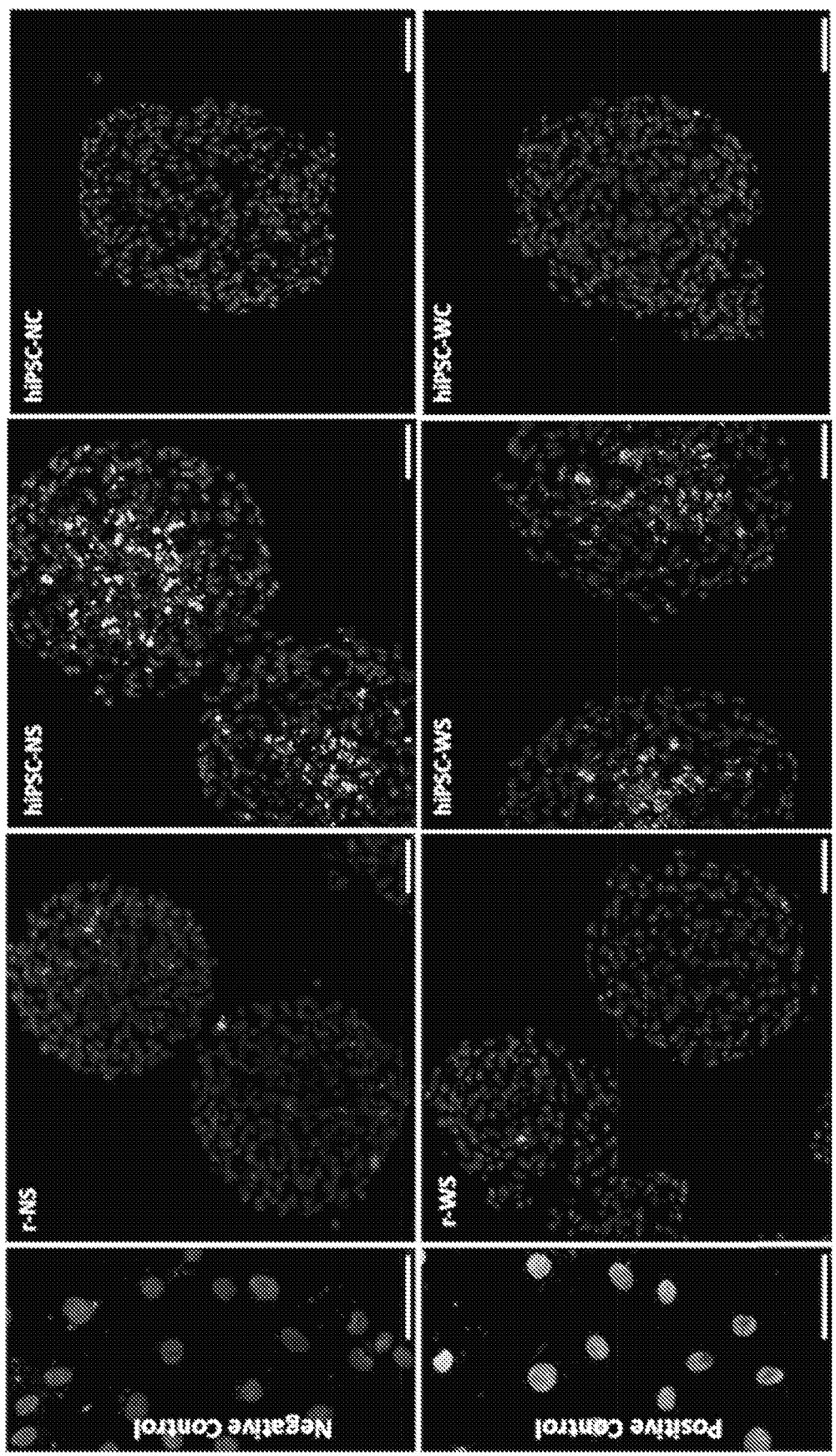

FIG. 10. TUNEL staining for the frozen sections of spheroids. Medium grey color is DAPI staining for nuclei, which indicates the viable cells in spheroids. Light grey color is TUNEL staining for fragments of DNA, which indicates the apoptosis of cells in spheroids. Scale bars: 50 µm.

Figure 11:
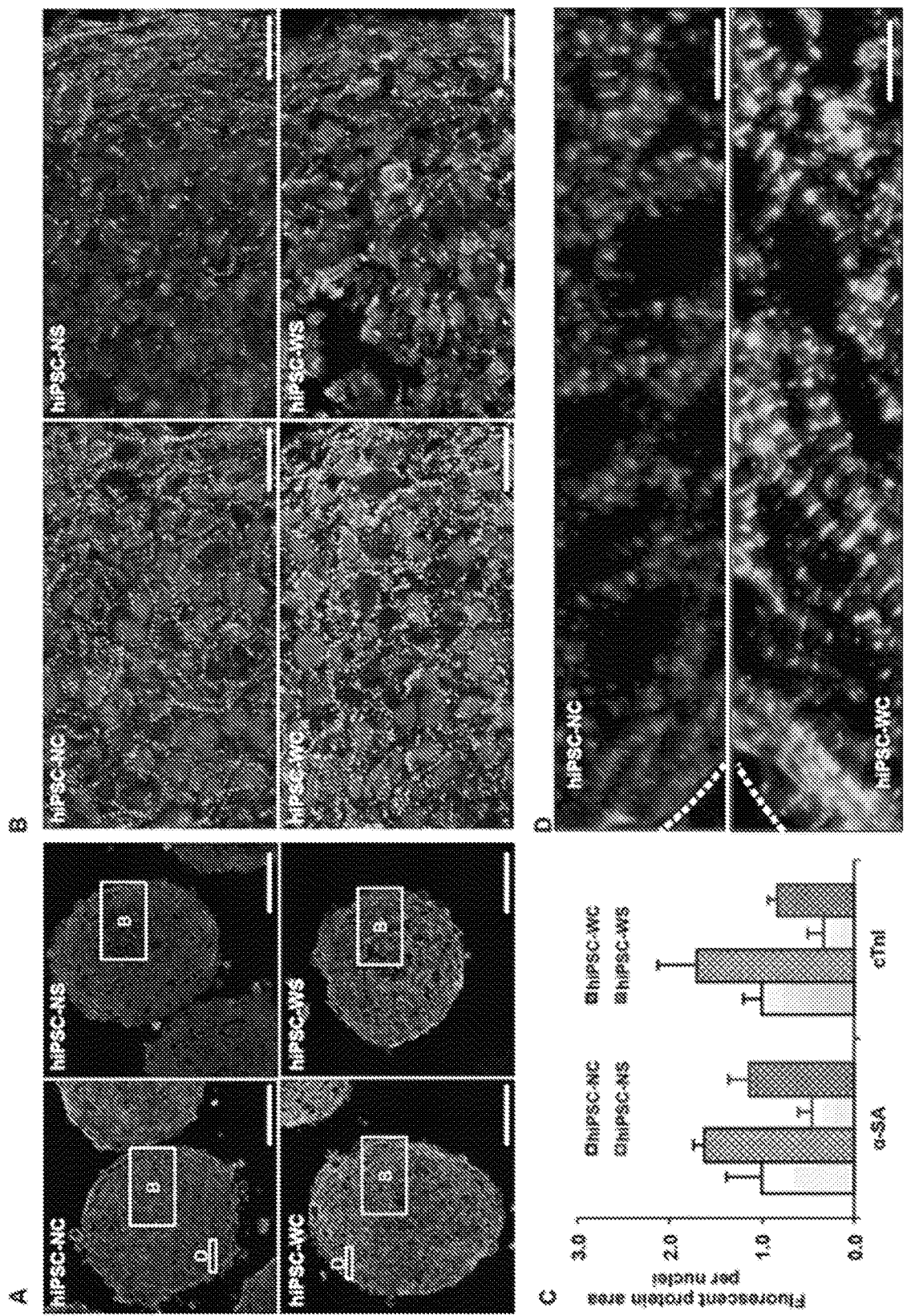

FIG. 11. Cellular organization of hiPSC-derived cardiomyocyte spheroid cross-sections after 7 days of treatment. (A) Low and (B) high magnification confocal images (light grey, α-sarcomeric actinin (α-SA); medium grey, troponin I; medium grey, DAPI nuclear stain) that display the difference in the sarcomere expression and organization within spheroids. (C) Protein expression analysis based on fluorescent signal-covered area per nuclei normalized over hiPSC-NC expression; n=3 picture regions; 75 µm×130 µm picture regions, at least containing >50 nuclei. (D) Characteristic images of hiPSC-NC and hiPSC-WC treatments to reveal differences in sarcomere alignment of each whole spheroid (dotted line=spheroid border). hiPSC-NC=human induced pluripotent stem cell cardiac spheroids, no e-SiNWs, no stimulation; hiPSC-NS=human induced pluripotent stem cell cardiac spheroids, no e-SiNWs, with stimulation; hiPSC-WC=human induced pluripotent stem cell cardiac spheroids, with e-SiNWs, no stimulation; hiPSC-WS=human induced pluripotent stem cell cardiac spheroids, with e-SiNWs, with stimulation. Error bars represent standard deviation. Scale bars: (A)=100 µm; (B)=20 µm; (D)=5 µm.

Figure 12:
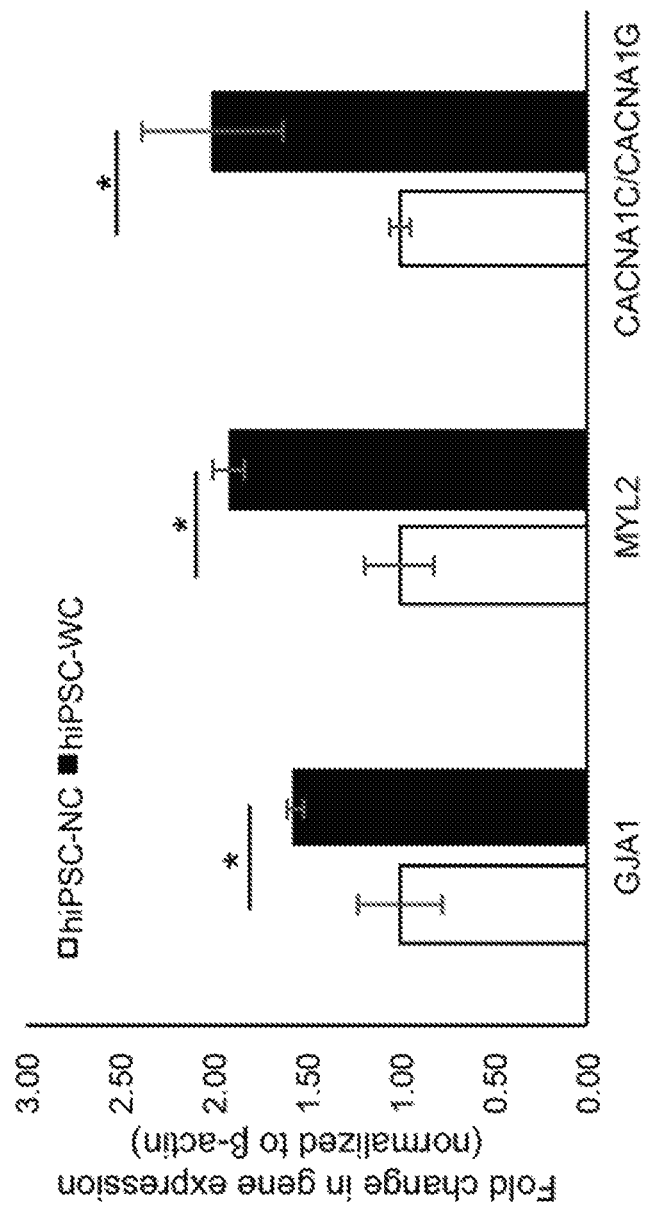

FIG. 12. qPCR analysis of mRNA expression of conductive and contractile genes in hiPSC-NC and hiPSC-WC spheroids. GJA1—connexin-43; MYL2—myosin light chain ventricular isoform; CACANA1C—calcium L-type channel; CACNA1G—calcium T-type channel. Asterisks (*) represent statistical significance with p<0.05; error bar represents standard deviation, n=3.

Figure 13:
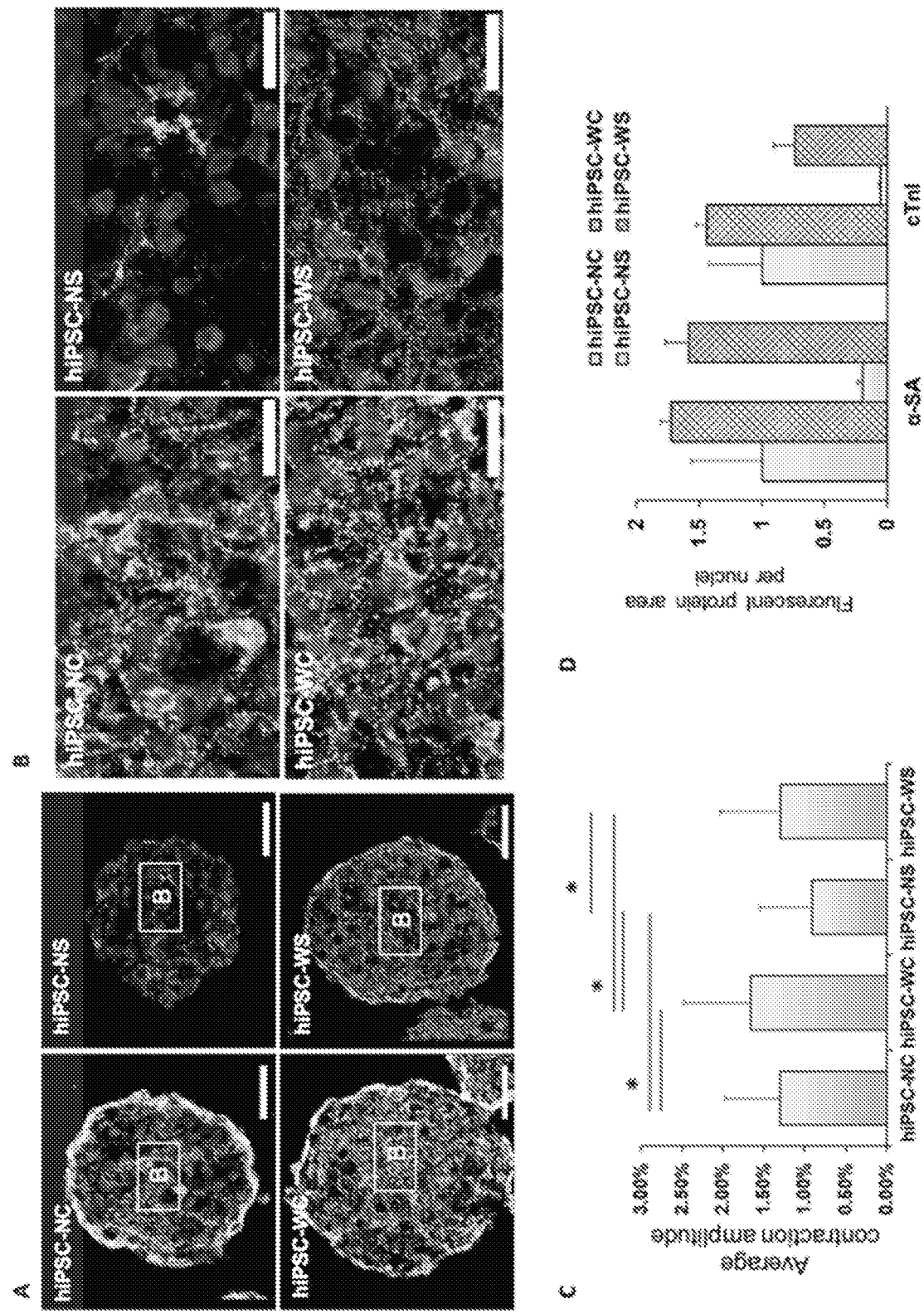

FIG. 13. Analysis of hiPSC-derived cardiomyocyte spheroids after 3 weeks culture. (A) Low and (B) high magnification confocal images (light grey, α-sarcomeric actinin (α-SA); medium grey, troponin I; medium grey, DAPI nuclear stain) that display the difference in the sarcomere expression and organization within spheroids after 21 days in culture. (C) Average contraction amplitude (i.e., fractional area change) of spontaneously beating spheroids with and without e-SiNWs and/or electrical stimulation after 21 days in culture; n=6 spheroids per condition. (D) Protein expression analysis based on fluorescent signal-covered area per nuclei normalized over hiPSC-NC expression; n=3 picture regions; 40 μm×40 μm picture regions. hiPSC-NC=human induced pluripotent stem cell cardiac spheroids, no e-SiNWs, no stimulation; hiPSC-NS=hiPSC cardiac spheroids, no e-SiNWs, with stimulation; hiPSC-WC=hiPSC cardiac spheroids, with e-SiNWs, no stimulation; hiPSC-WS=hiPSC cardiac spheroids, with e-SiNWs, with stimulation. Asterisk (*) represents statistical difference between groups with p<0.05; error bar represents standard deviation. Scale bars: (A)=50 μm; (B)=20 μm.

Figure 14:
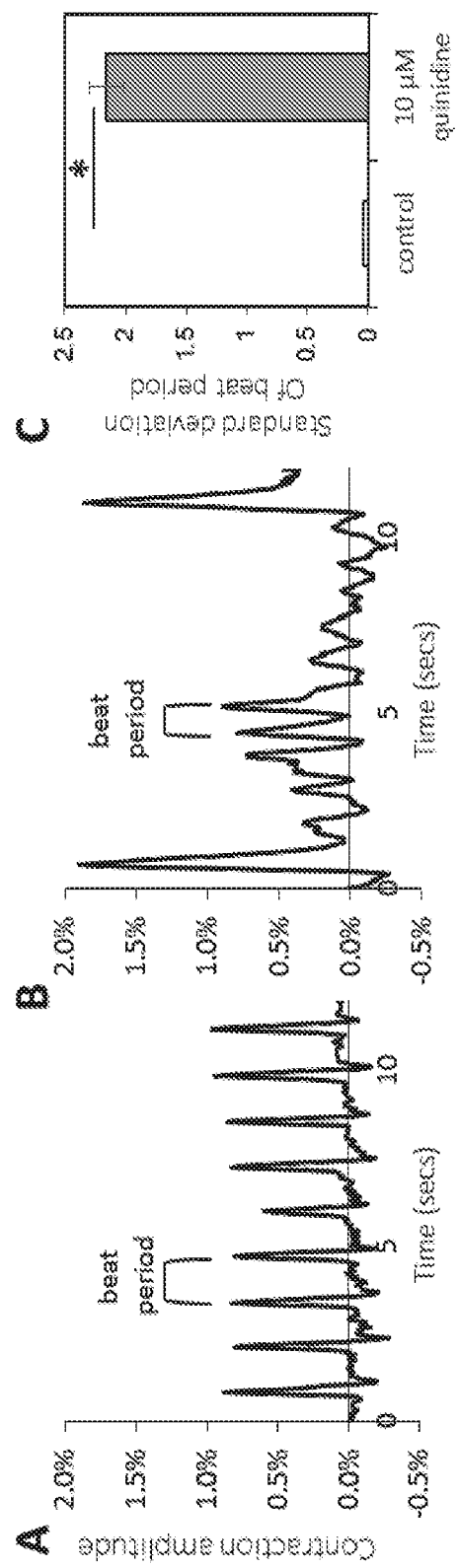

FIG. 14. Functional detection of arrhythmia in cardiac microtissues with semiconductor nanomaterials. (A) Representative contraction profile of contraction amplitude (i.e., fractional area change) of the microtissues in control media. (B) Representative contraction profile of the microtissues 20 mins after addition of 10 μM quinidine solution. (C) Standard deviation of beat period (sec) between control and 10 μM quinidine as a functional metric for arrhythmia detection.

DETAILED DESCRIPTION

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value, such as an amount or concentration and the like, is meant to refer to variations of up to ±20% of the specified value, such as, but not limited to, ±10%, ±5%, ±1%, ±0.5%, or even ±0.1% of the specified value, as well as the specified value. For example, "about X" where X is the measurable value, is meant to include X as well as variations of ±20%, ±10%, ±5%, ±1%, ±0.5%, or even ±0.1% of X. A range provided herein for a measurable value may include any other range and/or individual value therein.

According to some embodiments of the present invention, provided herein are tissues comprising a semiconductor nanomaterial. "Semiconductor nanomaterial" refers to a nanoscale semiconductor material that has dimensions (e.g., length, width, and/or diameter) that are measurable in nanometers and/or microns. In some embodiments, a tissue of the present invention comprises an n-type semiconductor nanomaterial and/or p-type semiconductor nanomaterial. The semiconductor nanomaterial may be biocompatible and/or biodegradable.

In some embodiments, the semiconductor nanomaterial may comprise a silicon nanomaterial. The silicon nanomaterial may comprise phosphorus and/or borane. In some embodiments, the silicon nanomaterial may comprise a phosphorous-doped silicon nanomaterial and/or a boron-doped silicon nanomaterial. The silicon nanomaterial may be a silicon nanowire and/or nanotube. In some embodiments, the silicon nanomaterial may have a silicon:phosphorous ratio in a range of about 10:1 to about 10000:1 and/or a silicon:borane ratio in a range of about 10:1 to about 10000:1. In some embodiments, a silicon nanomaterial may have a silicon:phosphorous ratio and/or a silicon:borane ratio of about 10:1, 25:1, 50:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1. In some embodiments, the silicon nanomaterial may have a silicon:phosphorous ratio and/or a silicon:borane ratio of about 500:1.

In some embodiments, the semiconductor nanomaterial may have a length of about 20 μm or less. For example, the semiconductor nanomaterial may have a length of about 20, 19, 18, 17, 16, 15, 14, 13, 12, 11, 10, 9, 8, 7, 6, 5, 4, 3, 2, 1, or 0.5 μm or less. In some embodiments, the semiconductor nanomaterial may have a length of about 1 μm to about 20 μm. In some embodiments, the semiconductor nanomaterial may have a length of about 10 μm. In some embodiments, the semiconductor nanomaterial may have a width and/or diameter of about 200 nm or less. For example, the semiconductor nanomaterial may have a width and/or diameter of about 200, 190, 180, 170, 160, 150, 140, 130, 120, 110, 100, 90, 80, 70, 60, 50, 40, 30, 20, 10, 9, 8, 7, 6, 5, 4, 3, 2, or 1 nm or less. In some embodiments, the semiconductor nanomaterial may have a width and/or diameter of about 10 nm to about 200 nm. In some embodiments, the semiconductor nanomaterial may have a width and/or diameter of about 100 nm.

The semiconductor nanomaterial may have any suitable conductivity. In some embodiments, a semiconductor nanomaterial may have a conductivity in a range of about 0.001 µS/µm to about 2000 µS/µm, such as, for example, about 0.01 µS/µm to about 1000 µS/µm, about 1 µS/µm to about 2000 µS/µm, or about 10 µS/µm to about 500 µS/µm. In some embodiments, a semiconductor nanomaterial may have a conductivity of about 0.001, 0.005, 0.01, 0.05, 0.1, 0.5, 1, 5, 10, 25, 50, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, or 2000 µS/µm.

A tissue of the present invention may comprise a semiconductor nanomaterial in an amount of about 0.00001% to about 1% by weight of the semiconductor nanomaterial per volume of the tissue. In some embodiments, the tissue may comprise a semiconductor nanomaterial in an amount of about 0.00001%, 0.00002%, 0.00003%, 0.00004%, 0.00005%, 0.00006%, 0.00007%, 0.00008%, 0.00009%, 0.0001%, 0.0002%, 0.0003%, 0.0004%, 0.0005%, 0.0006%, 0.0007%, 0.0008%, 0.0009%, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% by weight of the semiconductor nanomaterial per volume of the tissue. In some embodiments, the semiconductor nanomaterial may be present in an amount sufficient to promote and/or induce synchronized contraction of cells (e.g., muscle cells, such as, for example, cardiac cells) present in the tissue. In some embodiments, the semiconductor nanomaterial may promote and/or induce structural and/or contractile maturation in cells (e.g., muscle cells, such as, for example, cardiac cells) present in the tissue. The semiconductor nanomaterial may promote and/or induce cardiac tissue formation and/or cardiac cell maturation, optionally without a tissue scaffold (e.g., a polymer and/or hydrogel).

A tissue of the present invention may comprise muscle cells (e.g., cardiac cells) and a semiconductor nanomaterial. In some embodiments, the muscle cells may be cardiac cells. The cardiac cells may comprise cardiomyocytes and/or cardiac fibroblasts. In some embodiments, the cardiac cells are cardiomyocytes. The tissue may further comprise vascular cells such as, for example, endothelial cells.

In some embodiments, the tissue may be a two-dimensional or three-dimensional tissue. A tissue of the present invention may be a microtissue. In some embodiments, the tissue may be a spheroid (i.e., a spherically shaped tissue), an aggregate, and/or a patch. The spheroid may be a prolate spheroid or an oblate spheroid. The center or middle of a spheroid may be hollow or may comprise one or more cells (e.g., 1, 2, 3, 4, 5, 10, 20, 30, 40, 50, 100, 200, etc.).

A tissue of the present invention (e.g., a microtissue and/or spheroid) may have any suitable thickness, length, width, and/or diameter, such as, for example a thickness, length, width and/or diameter ranging from about 10 µm to about 50,000 µm, such as, but not limited to, from about 10 µm to about 900 µm, about 100 µm to about 700 µm, about 300 µm to about 600 µm, about 400 µm to about 500 µm, about 1,000 µm to about 10,000 µm, about 2,000 µm to about 50,000 µm, about 25,000 µm to about 40,000 µm, or 3,000 µm to about 15,000 µm. In some embodiments, a tissue may have a thickness, length, width, and/or diameter of about 10 µm, 25 µm, 50 µm, 100 µm, 200 µm, 300 µm, 400 µm, 500 µm, 600 µm, 700 µm, 800 µm, 900 µm, 1,000 µm, 5,000 µm, 10,000 µm, 15,000 µm, 20,000 µm, 25,000 µm, 30,000 µm, 35,000 µm, 40,000 µm, 45,000 µm, or 50,000 µm. In some embodiments, a plurality of tissues are generated according to embodiments of the present invention and the thickness, length, width, and/or diameter of the tissues may vary by less than about 20%, 19%, 18%, 17%, 16%, 15%, 14%, 13%, 12%, 11%, 10%, 9%, 8%, 7%, 6%, 5%, 4%, 3%, 2%, or 1%.

In some embodiments, a tissue of the present invention may be a tissue engineered construct. In some embodiments, the tissue may be scaffold-free. "Scaffold-free" as used herein means that the tissue does not comprise a scaffold, such as, for example, a hydrogel and/or a polymer. Thus, in some embodiments, a tissue of the present invention does not include a scaffold.

A tissue of the present invention may comprise an electrically conductive network and/or may exhibit synchronized electrical signal propagation within the tissue. In some embodiments, the tissue may exhibit increased functional assembly of the cells (e.g., cardiac cells) compared to the functional assembly of cells in a tissue prepared using and/or derived from a conventional tissue culture method (e.g., a tissue culture method that does not include a semiconductor nanomaterial or a monolayer of cardiac cells derived from stem cells). In some embodiments, the tissue may comprise cardiac cells and the tissue may exhibit increased cardiac specific functions compared to a cardiac tissue prepared using and/or derived from a conventional tissue culture method (e.g., a tissue culture method that does not include a semiconductor nanomaterial or a monolayer of cardiac cells derived from stem cells). A tissue of the present invention may have and/or exhibit increased functional assembly of cells and/or increased cardiac specific functions by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, or more compared to the functional assembly of cells in and/or cardiac specific functions of a tissue prepared using and/or derived from a conventional tissue culture method (e.g., a tissue culture method that does not include a semiconductor nanomaterial or a monolayer of cardiac cells derived from stem cells).

In some embodiments, a tissue of the present invention may be a cardiac tissue. The tissue (e.g., cardiac tissue) may comprise the adult isoform of myosin protein. In some embodiments, the cells of the tissue (e.g., cardiac tissue) may express contractile proteins, such as, for example, cardiac α-sarcomeric actinin (α-SA), cardiac troponin I (cTnI), cardiac troponin T (cTnT), myosin heavy chain α/β, and/or myosin light chain (ventricle/atrial). In some embodiments, the cells of the tissue (e.g., cardiac tissue) may express conductive channel genes, such as, for example, GJA1 (Cx-43), CACNA1C (L-type), CACNA1G (T-type), KCNJ2 (inward rectifier), HCN4, SCN5A, RYR2, ATP2A2, and/or KCNH2 (hERG channel) and/or contractile genes, such as, for example, ventricular and/or atrial myosin light chain (MYL2 and/or MYL4), alpha and/or beta myosin heavy chain (MYH6 and/or MYH7), and/or fetal and/or adult isoforms of troponin I (TNNI1 and/or TNNI3). In some embodiments, a tissue (e.g., cardiac tissue) of the present invention may exhibit increased expression of a contractile gene (e.g., MYL2) compared to a tissue (e.g., cardiac tissue) derived from a conventional tissue culture method (e.g., a tissue culture method that does not include a semiconductor nanomaterial or a monolayer of cardiac cells derived from stem cells). For example, the expression of a contractile gene (e.g., MYL2) in a tissue (e.g., cardiac tissue) of the present invention may be increased by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, or more compared to the expression of the contractile gene (e.g., MYL2) in a tissue (e.g., cardiac tissue) prepared using and/or derived from a conventional method.

In some embodiments, the cells of the tissue (e.g., cardiac tissue) of the present invention may comprise mature calcium handling channels. In some embodiments, the cells of the tissue (e.g., cardiac tissue) may have an increased sarcomere length and/or Z-band width compared to a tissue (e.g., cardiac tissue) prepared using and/or derived from a conventional tissue culture method (e.g., a tissue culture method that does not include a semiconductor nanomaterial or a monolayer of cardiac cells derived from stem cells). For example, the cells of the tissue (e.g., cardiac tissue) may have a sarcomere length and/or Z-band width that is increased by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, or more compared to the sarcomere length and/or Z-band width of a tissue (e.g., cardiac tissue) prepared using and/or derived from a conventional method.

In some embodiments, the alignment of the Z-band in cells of a tissue (e.g., cardiac tissue) of the present invention is substantially similar to native cells in a tissue (e.g., native cardiac cells) in a tissue (e.g., cardiac tissue). "Native cells" and "native cardiac cells" refer to cells (e.g., cardiac cells) that are formed naturally in vivo and not by a tissue culture method.

In some embodiments, a tissue (e.g., cardiac tissue) of the present invention may exhibit synchronized and/or increased contraction compared to a tissue (e.g., cardiac tissue) prepared using and/or derived from a conventional tissue culture method (e.g., a tissue culture method that does not include a semiconductor nanomaterial or a monolayer of cardiac cells derived from stem cells). For example, a tissue (e.g., cardiac tissue) may, exhibit increased contraction by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300% or more compared to a tissue (e.g., cardiac tissue) prepared using and/or derived from a conventional tissue culture method (e.g., a tissue culture method that does not include a semiconductor nanomaterial or a monolayer of cardiac cells derived from stem cells). In some embodiments, a tissue (e.g., cardiac tissue) of the present invention may exhibit synchronized and/or increased contraction compared to a tissue (e.g., cardiac tissue) prepared using and/or derived from a conventional tissue culture method as determined by the change in the fractional area of the tissue. In some embodiments, a tissue (e.g., cardiac tissue) of the present invention has a change in fractional area of at least about 2%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300% or more compared to a tissue (e.g., cardiac tissue) prepared using and/or derived from a conventional tissue culture method (e.g., a tissue culture method that does not include a semiconductor nanomaterial or a monolayer of cardiac cells derived from stem cells).

A tissue of the present invention may comprise mammalian cells, such as, human and/or non-human (e.g., rat, hamster, mouse, dog, cat, monkey, horse, pig, etc.) cells. In some embodiments, the tissue comprises human cells. A tissue of the present invention may be used for therapeutic purposes, including veterinary purposes, and/or may be used for research and/or drug screening purposes.

According to some embodiments of the present invention, provided herein are methods of preparing a tissue, such as, for example, a cardiac tissue. A method of the present invention may provide a tissue (e.g., a cardiac tissue) as described herein. In some embodiments, a method of the present invention may produce functional mature muscle cells (e.g., functional mature cardiac cells). In some embodiments, a method of the present invention may mature stem cells into contractile muscle tissue. In some embodiments, a method of the present invention may mature stem cells into contractile cardiac microtissue. A method of the present invention may produce and/or create a conductive microenvironment that may produce and/or create a functional mature cardiac microtissue, such as, for example, a contractile cardiac microtissue.

A method of the present invention may comprise seeding a substrate with a cell suspension comprising a plurality of cells (e.g., cardiac cells and/or vascular cells) and a semiconductor nanomaterial to form a cell culture, thereby preparing a tissue (e.g., a cardiac tissue). In some embodiments, the cell suspension may have a concentration of cardiac cells and/or vascular cells in a range of about $1\times10^3$ to about $1\times10^7$ cells/mL. The cardiac cells may be cardiomyocytes and/or cardiac fibroblasts. The cardiomyocytes may be derived from human induced pluripotent stem cells, multipotent mesodermal progenitors, and/or cardiac progenitor cells. In some embodiments, the cardiac cells are cardiomyocytes that may be derived from human induced pluripotent stem cells. The vascular cells may be and/or derived from endothelial cells and/or endothelial progenitor cells.

In some embodiments, the cell suspension may comprise muscle cells (e.g., cardiac cells) and the semiconductor nanomaterial in a ratio in a range of about 0.5:1 to about 100:1 (number of cells:number of semiconductor nanomaterials). In some embodiments, the cell suspension may comprise muscle cells (e.g., cardiac cells) and the semiconductor nanomaterial in a ratio of about 0.5:1, 1:1, 5:1, 10:1, 25:1, 50:1, 75:1, 100:1, 1:100, 1:75, 1:50, 1:25, 1:10, 1:5, or 1:0.5. In some embodiments, the cell suspension may comprise muscle cells (e.g., cardiac cells) and the silicon nanomaterial in a ratio of about 1:1.

The method may further comprise culturing the cell culture comprising the plurality of cells (e.g., cardiac cells and/or vascular cells) on the substrate in the presence of the semiconductor nanomaterial. In some embodiments, the substrate may comprise a plurality of microwells. The substrate may comprise any suitable material, such as, for example, agarose gel, polyethylene glycol, alginate, hyaluronic acid, polyacrylic acid, polyacrylic amide, polyvinyl alcohol, polyhydroxyethyl methacrylate, methacrylated dextrans, poly(N-isopropylacrylamide), and any combination thereof. In some embodiments, the substrate and/or microwell(s) may comprise any suitable unfouling hydrogel, such as, for example, agarose gel, polyethylene glycol, alginate, hyaluronic acid, polyacrylic acid, polyacrylic amide, polyvinyl alcohol, polyhydroxyethyl methacrylate, methacrylated dextrans, poly(N-isopropylacrylamide), and any combination thereof.

A method of the present invention may comprise a two or three dimensional culture in the presence of the semiconductor nanomaterial. In some embodiments, the method does not make use of a tissue scaffold (e.g., a polymer and/or hydrogel). For example, in some embodiments, the substrate may be scaffold-free.

The culturing step may be carried out using methods known to those knowledgeable in the field. After seeding a substrate with a cell suspension comprising a plurality of cells (e.g., cardiac cells) and a semiconductor nanomaterial, a tissue may be produced according to embodiments of the present invention. A plurality of cells and/or a tissue may be cultured on a substrate for any desired period of time, such as, but not limited to, hours, days, weeks, or months. In some embodiments, the plurality of cells and/or tissue are cultured for about 1, 2, 3, 4, 5, 6, or 7 days, or about 1, 2, 3, 4, 5, 6, 7, 8, 9, 10, or 11 or more weeks.

Cell culture media suitable for the methods of the present invention are known in the art and include, but are not limited to, Dulbecco's Modified Eagle's Medium (DMEM), Dulbecco's Modified Eagle's Medium high glucose (DMEM-H), McCoy's 5A Modified Medium, RPMI, Ham's media, Medium 199, mTeSR, and so on. The cell culture medium may be supplemented with additional components such as, but not limited to, vitamins, minerals, salts, growth factors, carbohydrates, proteins, serums, amino acids, attachment factors, cytokines, growth factors, hormones, antibiotics, therapeutic agents, buffers, etc. The cell culture components and/or conditions may be selected and/or changed during the methods of the present invention to enhance and/or stimulate certain cellular characteristics and/or properties. Examples of seeding methods and cell culturing methods are described in U.S. Pat. Nos. 5,266,480, 5,770,417, 6,537,567, and 6,962,814 and Oberpenning et al. "De novo reconstitution of a functional mammalian urinary bladder by tissue engineering" *Nature Biotechnology* 17:149-155 (1999), which are incorporated herein by reference in their entirety.

The cell seeding and/or culturing may be carried out in a sterile environment using equipment and methods known in the art. In some embodiments, the temperature of the cell seeding and/or culturing environment is from about 25° C. to about 40° C. or any range therein, such as from about 30° C. to about 40° C. or from about 35° C. to about 40° C. In some embodiments, the temperature of the cell culturing environment is about 37° C. The cell culturing environment may be at atmospheric pressure, reduced pressure (e.g., vacuumized pressure), high pressure, and/or any combination thereof. In some embodiments, the pressure of the cell culturing environment is atmospheric pressure. In some embodiments, the cell culturing steps are carried out in an atmosphere of from about 1% to about 20% carbon dioxide ($CO_2$) or any range therein, such as from about 5% to about 10% or from about 5% and about 15% $CO_2$. In some embodiments, cell culturing is carried out in an atmosphere of from about 5% to about 10% $CO_2$. Other gases, such as, but not limited to, nitrogen and/or oxygen, may be added to the cell seeding and/or culturing atmosphere. In some embodiments, one or more gases may be used to obtain and/or maintain the desired atmosphere (e.g., to maintain the desired oxygen and/or carbon dioxide levels).

A method of the present invention may further comprise electrically stimulating the cell culture and/or tissue after a given period of time. For example, the cell culture and/or tissue may be electrically stimulated after 1, 5, 10, 12, or 20 hour(s), or 1, 2, 3, 4, 5, 6, 7, 8, 9, 10 day(s), or 1, 2, 3, 4 week(s), or more in culture and/or after seeding. In some embodiments, the cell culture and/or tissue may be electrically stimulated at about 1 day to about 5 days or about 1 day to about 2 weeks after seeding the substrate with the cell suspension.

The cell culture and/or tissue may be electrically stimulated in a range of about 10 V to about 20 V at about 0.5 Hz to about 2 Hz every 0.5 ms to 10 ms. In some embodiments, the cell culture and/or tissue may be electrically stimulated at about 15 V, 1 Hz, every 2 ms. The cell culture and/or tissue may be electrically stimulated for any duration of time, such as for example for about 1, 2, 3, 4, 5, 6, 7, 8, 9, 10 day(s), or 1, 2, 3, 4, 5, 6, 7, 8, 9 week(s), or 1, 2, 3 month(s), or more. In some embodiments, the cell culture and/or tissue may be electrically stimulated for about 1 day to about 2 weeks, about 1 day to about 2 months, about 2 days to about 1 week, or about 1 week to about 1 month.

Another aspect of the present invention comprises a method of using a tissue of the present invention. In some embodiments, a tissue of the present invention may be used for drug screening, such as, for example, in vitro drug screening. In some embodiments, a method of screening a compound (e.g., a chemical and/or biological compound) or composition is provided, the method including introducing and/or contacting the compound or composition to a tissue of the present invention. The method may further include detecting a response to the compound or composition. A positive response may indicate that the compound or composition is active when introduced to and/or in contact with the tissue, and a negative response may indicate that the compound or composition is inactive when introduced to and/or in contact with the tissue. In some embodiments, the method may screen for efficacy, toxicity, penetration, irritation, and/or other metabolic and/or physiological activity of the compound or composition.

In some embodiments, a method of treating a subject may be provided, the method comprising introducing a tissue of the present invention into the subject. The subject may be a subject in need thereof, such as, for example, a subject with heart failure and/or cardiac damage. In some embodiments, the tissue may be a cardiac tissue. The tissue, after introduction into the subject, may further differentiate, grow, and/or be incorporated into the subject's existing tissue. In some embodiments, a tissue of the present invention may be used in a cell transplantation and may optionally improve the outcome of the cell transplantation compared to if a tissue prepared not in accordance a method of the present invention were utilized (e.g., a tissue culture method that does not include a semiconductor nanomaterial or a monolayer of cardiac cells derived from stem cells). According to some embodiments of the present invention, a tissue of the present invention may be suitable for in vivo transplantation into a subject to treat cardiac disease and/or to repair a cardiac tissue. In some embodiments, a tissue of the present invention may be used in and/or for cardiac cell therapy. In some embodiments, a tissue may be transplanted into an infarcted heart of a subject.

In some embodiments, a tissue used to treat a subject and/or to test for drug screening purposes for a subject may be formed and/or prepared from autologous cells. In some embodiments, a tissue used to treat a subject and/or to test for drug screening purposes for a subject may be formed and/or prepared from heterologous cells.

The present invention is explained in greater detail in the following non-limiting Examples.

EXAMPLES

Example 1

It is demonstrated that the incorporation of a trace amount (i.e., ~0.004% w/v) of electrically conductive silicon nanowires (e-SiNWs) in otherwise scaffold-free cardiac spheroids can form an electrically conductive network, leading to synchronized and significantly enhanced contraction (i.e., >55% increase in average contraction amplitude), resulting in significantly more advanced cellular structural and contractile maturation.

Figure 1:
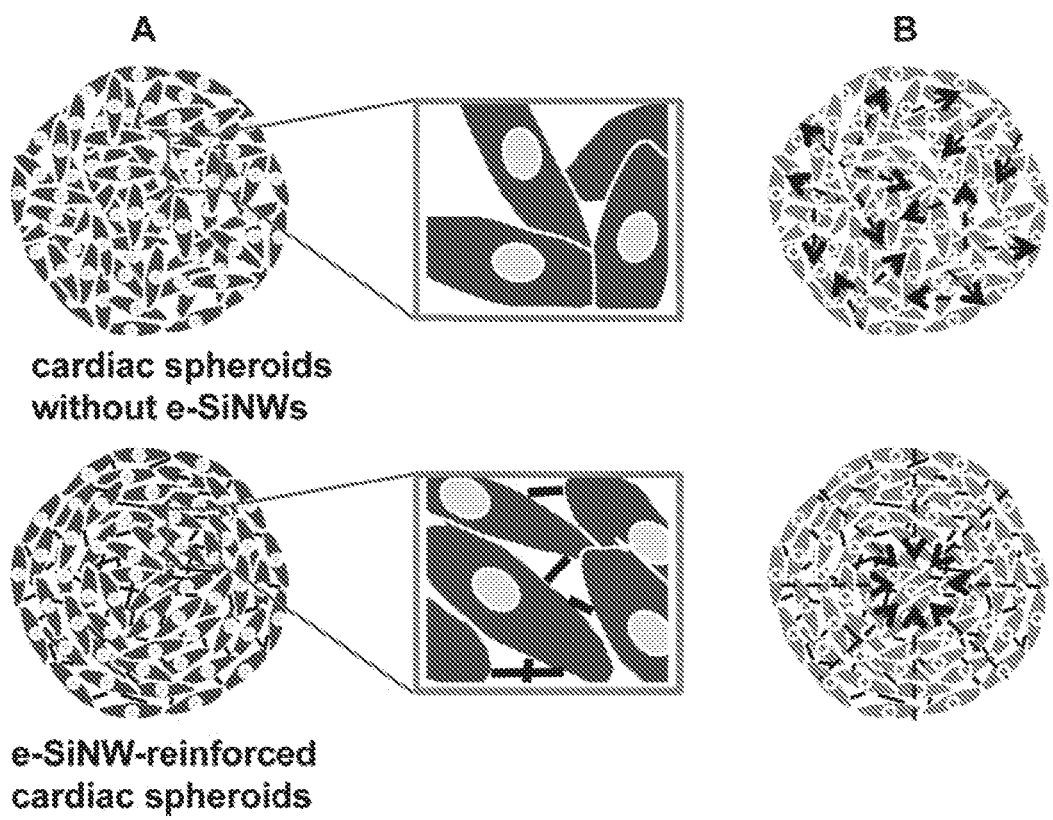
FIG. 1. Schematic overview of e-SiNWs reinforced cardiac spheroids. (A) Structure of cardiac spheroids without (top) or with (bottom) e-SiNWs: cardiac cells (medium grey), nuclei (light grey), and e-SiNWs (black). e-SiNWs (bottom) can act as bridges to electrically connect cardiac cells and create electrically conductive microenvironments throughout the spheroids. (B) Cardiomyocytes in the cardiac spheroids without e-SiNWs (top) form electrically isolated small beating clusters with random contractions, whereas cardiomyocytes in the e-SiNWs reinforced cardiac spheroids can produce synchronized and enhanced contractions (bottom). Arrows represent the directions of contractile forces.

During embryonic development, environmental factors (e.g., extracellular matrix, growth factors, and mechanical and electrical stimulation) have major effects on the maturation of cardiomyocytes. To mimic the maturation process in vitro, hESC- and hiPSC-derived cardiomyocytes have been mixed with scaffolding materials (e.g., Matrigel and collagen type I gel) to prepare cardiac tissue-engineered constructs and then conditioned with electrical or mechanical stimulation. (4, 9-11) Although these scaffolds can provide tissue-like 3D microenvironments, current scaffolding materials lack the matched physical/chemical/biological properties with the native extracellular environments during heart development. On the other hand, scaffold-free, 3D cardiac spheroids have emerged as promising model systems to mimic cardiac tissues. (12, 13) Unlike in the myocardium, cardiomyocytes in the spheroids do not organize in a controlled manner and led to compromised, unsynchronized contractions. In this current study, it was investigated whether the incorporation of electrically conductive silicon nanowires (e-SiNWs) in cardiac spheroids would facilitate the formation of an electrically conductive network and provide synchronized and improved electrical/mechanical signals to advance structural and contractile maturation of the cardiomyocytes (FIG. 1 and FIG. 7).

This approach has the distinct advantage in that only a trace amount of e-SiNWs is utilized, minimizing the adverse effects of traditional scaffolds, such as unmatched physical/chemical/biological properties with the native extracellular environments during heart development. e-SiNWs were selected because of their controllable electrical conductivity, tunable dimensions, and convenient surface tailorability. (14, 15) Although SiNWs might not be well known as biocompatible materials, in vitro biocompatibility studies have shown no significant cytotoxic effects for both undoped and n-type SiNWs. (16) Further, the recent research showed SiNWs are biodegradable, and their degradation products are found mainly in the form of $Si(OH)_4$ and are metabolically tolerant in vivo. (17-21) This makes them advantageous over other nonbiodegradable, electrically conductive nanomaterials (e.g., gold nanowires, carbon nanotubes, and nanofibers), especially for potential in vivo applications.

Figure 2:
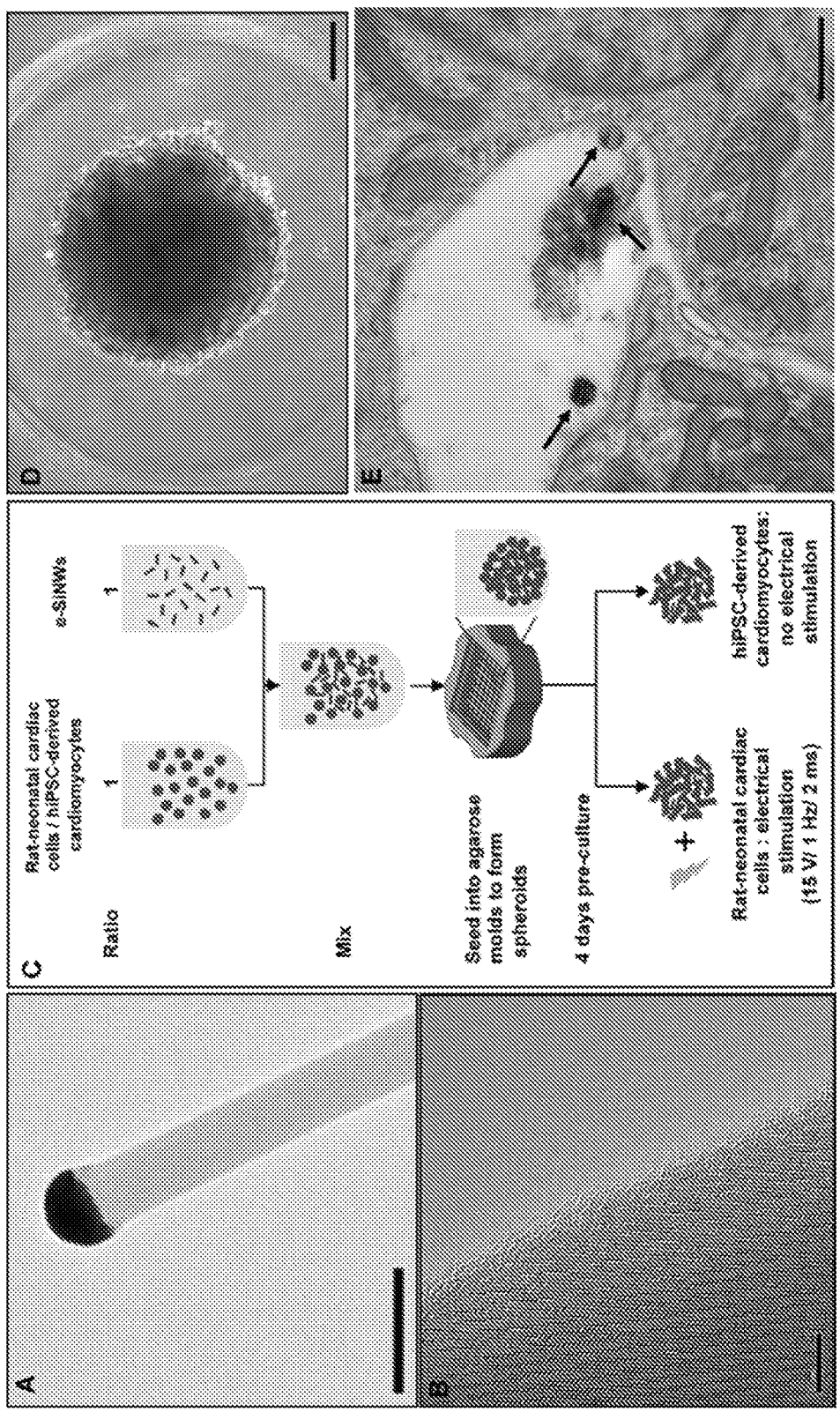
FIG. 2. Electrically conductive silicon nanowires (e-SiNWs) introduced to cardiac spheroids. (A) Transmission electron microscopy (TEM) image of an e-SiNW (diameter≈100 nm; length≈10 µm) and (B) high-resolution TEM image of the e-SiNW. (C) Schematic representation of spheroid fabrication using rat-neonatal cardiac cells or human induced pluripotent stem cell (hiPSC)-derived cardiomyocytes at a ratio 1:1 (number of cells:number of e-SiNWs) with or without electrical stimulation. (D) Bright field image of hiPSC spheroid with e-SiNWs. (E) TEM image of hiPSC spheroid with e-SiNWs, black arrow indicates the e-SiNWs located in the extracellular area. Scale bars: (A) 0.2 µm; (B) 5 nm; (D) 100 µm; (E) 500 nm.

In this study, n-type SiNWs (diameter≈100 nm; length≈10 µm; silane/phosphane=500) were prepared according to the previously established protocol (22) (FIG. 2, panels A and B). The doping ratio and diameter of the e-SiNWs were chosen to obtain a high conductivity (150-500 µS/µm) compared to cell culture medium (~1.75 µS/µm) and myocardium (~0.1 µS/µm) to create highly electrically conductive microenvironments within spheroids. (23, 24) The length of the SiNWs was selected to inhibit cell internalization. As shown in FIG. 2, panels C-E, both rat neonatal cardiac cells and human induced pluripotent stem cell-derived cardiomyocytes have been used to prepare e-SiNW-reinforced cardiac spheroids. The rat left-ventricle neonatal cardiac cells were utilized in the initial study due to their ready availability. They were mixed with e-SiNWs at a ratio of around 1:1 (number of cells/number of e-SiNWs) and seeded into agarose microwells to prepare e-SiNW-reinforced rat-neonatal cardiac spheroids (FIG. 2, panels C and 2D and FIG. 7). The ratio between e-SiNWs and cardiac cells was selected to minimize the interference of e-SiNWs on the self-assembly process of cardiac cells due to their high density and high stiffness (FIG. 8). Notably, TEM images of e-SiNW-reinforced cardiac spheroid indicated the e-SiNWs located in the extracellular space in the spheroids, which supported our selection of dimensions of e-SiNWs (FIG. 2, panel E).

Figure 3:
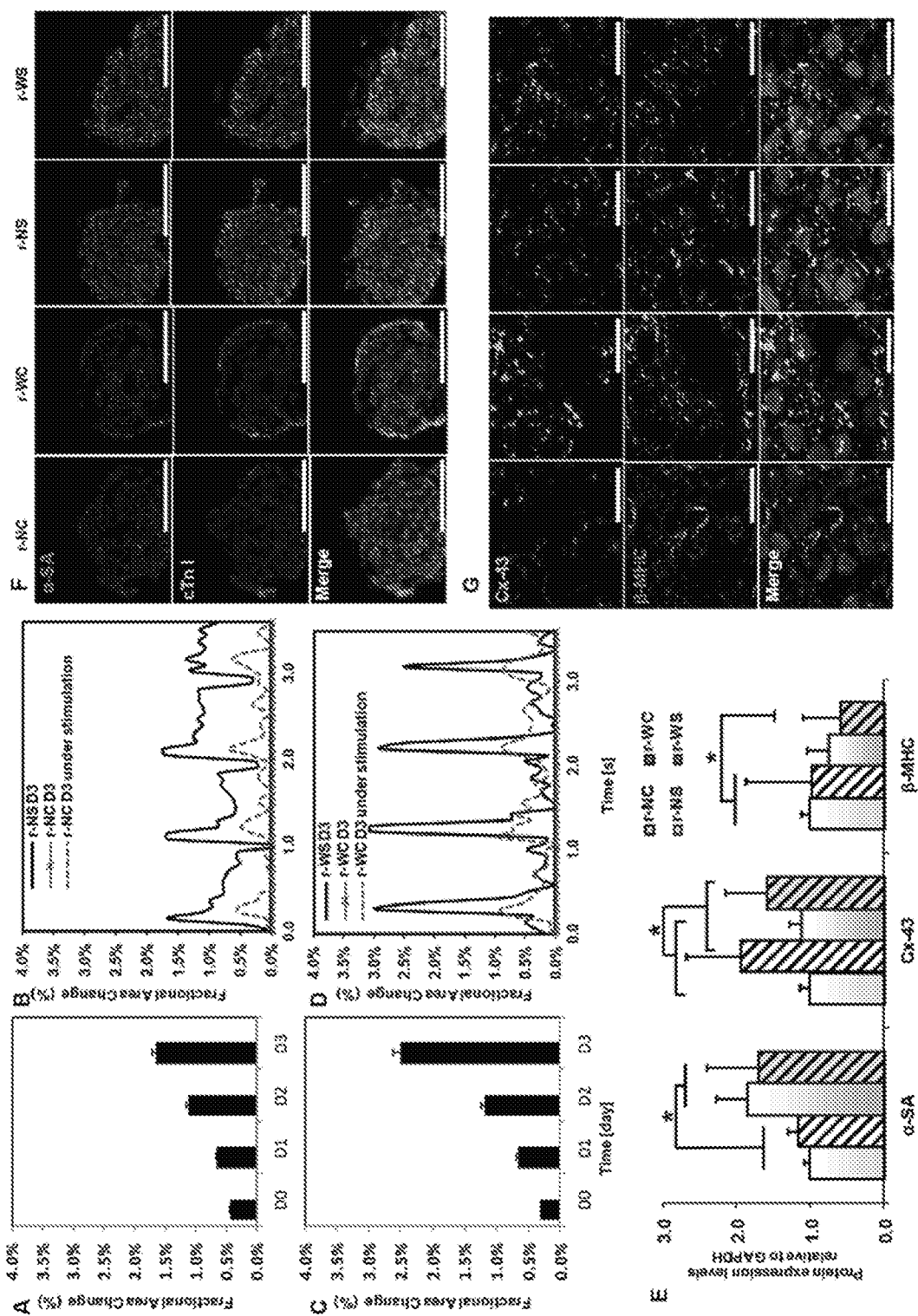
FIG. 3. Functional and structural analysis of rat-neonatal cardiac spheroids. (A) Averaged fractional area change (i.e., contraction amplitude) over 3 days for r-NS spheroids and (B) a characteristic beating profile on day 3 for r-NC, r-NC under stimulation during measurement, and r-NS spheroids. (C) Averaged fractional area change over 3 days for r-WS spheroids and (D) a characteristic beating profile on day 3 for r-WC, r-WC under stimulation during measurement, and r-WS spheroids. (E) Western blot analysis (averaged data of three separate experiments) of protein expression levels relative to GAPDH expression after 7 days with or without electrical stimulation normalized to the r-NC group. (F, G) Immunofluorescent staining of cardiac-specific contractile and conductive proteins for all groups after 7 days. r-NC=rat-neonatal cardiac spheroids, no e-SiNWs, no stimulation; r-NS=rat-neonatal cardiac spheroids, no e-SiNWs, with stimulation; r-WC=rat-neonatal cardiac spheroids, with e-SiNWs, no stimulation; r-WS=rat-neonatal cardiac spheroids, with e-SiNWs, with stimulation. n=6 spheroids per condition (A-D). Asterisks (*) represent statistical significance with p<0.05; error bars represent standard deviation. Scale bars: (F) 100 µm; (G) 20 µm.

Although few spontaneous contractions have been found in many rat-neonatal cardiac spheroids after 4 days in culture, both contraction frequency and amplitude can be significantly enhanced by electrical stimulation (FIG. 3, panels A-D). To recapitulate the electrical pulses of native myocardium, the spheroids were stimulated at 15 V at 1 Hz, 2 ms. (25) To independently investigate the effects of e-SiNWs and electrical stimulation, four samples have been prepared and examined: rat-neonatal cardiac spheroids without e-SiNWs and without electrical stimulation (i.e., r-NC spheroids), rat-neonatal cardiac spheroids with e-SiNWs but without electrical stimulation (i.e., r-WC spheroids), rat-neonatal cardiac spheroids without e-SiNWs but with electrical stimulation (i.e., r-NS spheroids), and rat-neonatal cardiac spheroids with e-SiNWs and with electrical stimulation (i.e., r-WS spheroids).

Video analysis revealed that the chronically stimulated spheroids (i.e., r-NS and r-WS spheroids) contract regularly and periodically, while the nonstimulated spheroids (i.e., r-NC and r-WC spheroids) did not contract consistently. As shown in FIG. 3, panels A-D, the average contraction amplitude gradually increased over time for the chronically stimulated spheroids (i.e., r-NS and r-WS) and was several-fold higher than the nonstimulated spheroids (i.e., r-NC and r-WC) with/without stimulation during measurement, which is consistent with the previous report. (25) When comparing r-NS spheroids with r-WS spheroids, significant improvements in the contraction amplitude and synchronization were found in the r-WS spheroids (FIG. 3 panels B and D), which indicates e-SiNWs can facilitate synchronized electrical signal propagation throughout the spheroids.

To understand the effects of e-SiNWs and chronic stimulation, the expressions of several key cardiac-specific proteins in all four different spheroids were examined using Western blotting and immunofluorescence staining (FIG. 3, panels E-G and FIG. 9, panels A and B). Among them, connexin-43 (i.e., Cx-43) forms gap junction channels that regulate electrical signal propagation between cardiomyocytes. (26, 27) Cardiac α-sarcomeric actinin (α-SA) and cardiac troponin I (cTnI) are cardiac-specific contractile proteins, and β-myosin heavy chain (β-MHC) is the neonatal isoform of myosin heavy chain in rat cardiomyocytes. (25) As shown in FIG. 3 panels E and F and FIG. 9, panels A and B, chronic stimulation can significantly increase the expressions and assembly of contractile proteins (e.g., α-SA and cTnI), in agreement with the previous report. (25) On the other hand, the incorporation of e-SiNWs led to enhanced expression and clustering of Cx-43 (FIG. 3, panels E and G), also consistent with the previous literature. (28-31) The combination of SiNWs and chronic stimulation can result in the reduced expression of β-MHC, which indicates a transition from the neonatal isoform of myosin protein to the adult isoform. (25) This could be attributed to the up-regulated Cx-43 expression (FIGS. 3 E and G) or the increased contraction amplitude (FIG. 3, panel D).

The results from rat-neonatal cardiac spheroids led to the development of hiPSC cardiac spheroids (i.e., cardiac spheroids prepared from hiPSC-derived cardiomyocytes, FIG. 2, panel C). Unlike the rat-neonatal cardiac spheroids, strong spontaneous contractions with consistent contraction frequency were found for the nonstimulated hiPSC cardiac spheroids. Notably, a significant decrease in contraction amplitude was found for electrically stimulated hiPSC-derived cardiac spheroids (i.e., hiPSC-NS and hiPSC-WS spheroids) (FIG. 4A). TUNEL staining (marker of early apoptosis) of the spheroid sections revealed significant increase in cell death at the center of hiPSC-NS and hiPSC-WS spheroids, whereas it was not in the r-NS and r-WS spheroids (FIG. 10). Given the similar sizes of the rat-neonatal and hiPSC cardiac spheroids, the increased cell death at the center of stimulated hiPSC-derived cardiomyocytes was attributed to the increased metabolic demands of the hiPSC-derived cardiomyocytes compared to rat-neonatal cardiac cells. (32-34) Accordingly, strong expression of the assembled cardiac contractile proteins (e.g., $\alpha$-SA and c-TnI) can only be found on the periphery of the hiPSC-NS and hiPSC-WS spheroids (FIGS. 11A, 11B).

On the other hand, the addition of e-SiNWs into hiPSC cardiac spheroids without electrical stimulation (i.e., hiPSC-WC spheroids) can lead to significant improvement in contraction amplitude and synchronization. As shown in FIG. 4A, the contraction amplitude of the hiPSC-WC spheroids averaged more than 55% higher than the hiPSC-NC spheroids from Day 1 to Day 7. The sharper peaks of fractional area change of the hiPSC-WC spheroids over the hiPSC-NC spheroids strongly indicated the enhanced contraction synchronization (FIGS. 4B, 4C). This is further supported by calcium transient imaging of whole spheroids (FIGS. 4D, 4E). The quantification of calcium imaging of spheroids revealed the hiPSC-WC spheroids have an increased overall amplitude ($F/F_0$) of calcium levels and an accelerated time to peak of the calcium transient (FIGS. 4F, 4G), which supported the enhanced synchrony during spontaneous contraction. The significant improvement in contraction amplitude and synchronization of hiPSC-WC spheroids is remarkable, considering only a trace amount of e-SiNWs (i.e., 0.004% w/v) was utilized to create e-SiNW-reinforced cardiac spheroids.

The enhanced contraction amplitude and synchronization of the hiPSC-WC spheroids resulted in improved functional maturation. As shown in FIGS. 5A-C and FIGS. 11C, 11D, the immunofluorescence staining indicated the significant increase in expression level and assembly of both conductive and contractile proteins (e.g., Cx-43, $\alpha$-SA, and cTnI) in the hiPSC-WC spheroids, which was further supported by the increased expression of conductive gene GJA1 (Cx-43) and contractile gene MYL2 (ventricle isoform of myosin light chain) (FIG. 12). In addition, FIGS. 4D-4G showed the improved peak calcium amplitude and the speed of calcium release, which suggest the improved calcium handling channels and indicates increased maturation. This is further supported by the increased ratio of gene expression of the calcium channel L-type/T-type subunits (CACNA1C/CACNA1G) (FIG. 12). The improved calcium handling properties can be attributed to the enhanced organization of the sarcomere structures in the hiPSC-WC spheroids. (35)

To confirm the effects of e-SiNW-reinforced 3D cell culture on the structural and contractile maturation of hiPSC-derived cardiomyocytes, monolayer cells were obtained from hiPSC cardiac spheroids by seeding them onto gelatin-coated substrates, which was thought to minimize dramatic stress usually associated with mechanical/enzymatic spheroid dissociation processes. Sarcomere length and Z-line width were measured as they were known as effective indicators of twitch force generated by cardiomyocytes (36, 37) (FIG. 6). As shown in FIGS. 6A-6C and 6G, cardiomyocytes harvested from both hiPSC-NC and hiPSC-WC spheroids showed significant improvement in Z-line width when compared to prespheroid hiPSC-derived cardiomyocytes. This indicates that 3D culture can provide supportive microenvironments for the maturation of hiPSC-derived cardiomyocytes. Moreover, the hiPSC-WC cardiomyocytes showed significant improvement in both sarcomere length and Z-line width when compared to the hiPSC-NC cardiomyocytes (FIGS. 6F, 6G). These improvements were attributed to the enhanced contraction of the hiPSC-WC spheroids. Notably, the alignment of Z-line in hiPSC-WC cardiomyocytes showed remarkable resemblance with adult rat cardiomyocytes (FIGS. 6C-6E and 6H). The increased sarcomere alignment in the hiPSC-WC spheroids was attributed to the e-SiNW-induced synchronized contractions (FIGS. 4B, 4C), which was hypothesized to provide an anisotropic mechanical environment to direct the assembly of contractile machinery of hiPSC-WC cardiomyocytes.

For the first time, a trace amount of e-SiNWs was incorporated into rat-neonatal and hiPSC cardiac spheroids to create electrically conducting microenvironments and induce synchronized and enhanced contraction, which was shown to promote structural and contractile maturation. A long-term culture (i.e., 3 weeks) was conducted to examine whether the addition of e-SiNWs into the hiPSC cardiac spheroids alone is sufficient to derive fully matured hiPSC-derived cardiomyocytes. The improvements in hiPSC-WC spheroids in contraction amplitude, expression level and assembly of contractile protein (e.g., $\alpha$-SA and cTnI) seen at Day 7 were maintained through Day 21 (FIG. 13). However, the extended culture did not result in further improvements in the maturation of hiPSC-derived cardiomyocytes. The sarcomere structure and nuclear shape in hiPSC-WC spheroids and hiPSC-NC spheroids at Day 21 resembled that of the Day 7 spheroids (FIGS. 5, 11 and 13). Additional chemical/physical stimuli (e.g., growth factors, miRNA, supporting cells) may be combined with e-SiNW-reinforced human cardiac spheroids to produce more matured hiPSC-cardiomyocytes. (35, 38)

Recently, nanocomposite scaffolds composed of electrically conductive nanomaterials and hydrogels have been developed for cardiac tissue engineering applications. (24, 29-31) The research reported here is the first demonstration of using nanoscale semiconductors to promote cardiac tissue formation and cardiomyocyte maturation without involving conventional scaffolding materials (e.g., polymers and hydrogels). Also, this research is the first example to directly utilize silicon-based nanomaterials for tissue engineering applications. The results here demonstrate that silicon-based nanomaterials can have major impacts in tissue engineering. Notably, e-SiNW induced synchronized contraction can be used in cell-based cardiac therapy, considering that arrhythmia caused by unsynchronized contraction is a major concern in cardiac surgery. (7, 8)

REFERENCES

1. Roger et al. J. Circulation 2011, 123 (4) e18-e209
2. Laflamme et al. Annu. Rev. Pathol. 2007, 2, 307-39
3. Mignone et al. C. E. Circ. J. 2010, 74 (12) 2517-26
4. Nunes et al. M. Nat. Methods 2013, 10 (8) 781-7
5. Lundy et al. Stem Cells Dev. 2013, 22 (14) 1991-2002

6. Lieu et al. Circ.: Arrhythmia Electrophysiol. 2013, 6 (1) 191-201
7. Shiba et al. Nature 2012, 489 (7415) 322-5
8. Chong et al. Nature 2014, 510 (7504) 273-277
9. Kensah et al. Eur. Heart J. 2013, 34 (15) 1134-46
10. Zhang et al. Biomaterials 2013, 34 (23) 5813-20
11. Mihic et al. Biomaterials 2014, 35 (9) 2798-2808
12. Desroches et al. Am. J. Physiol. 2012, 302 (10) H2031-42
13. Kelm et al. Tissue Eng. 2004, 10 (1-2) 201-14
14. Schmidt et al. Adv. Mater. 2009, 21, 2681-2702
15. Tian et al. Annu. Rev. Anal. Chem. 2013, 6, 31-51
16. Garipcan et al. Adv. Eng. Mater. 2011, 13, B3-B9
17. Jiang et al. ACS Appl. Mater. Interfaces 2009, 1 (2) 266-9
18. Nagesha et al. Adv. Mater. 2005, 17 (7) 921-924
19. Anderson et al. J. Phys. Status Solidi A 2003, 197 (2) 331-335
20. Zhou et al. Nano Lett. 2014, 14 (3) 1614-9
21. Tolli et al. Biomaterials 2014, 35 (29) 8394-405
22. Zheng et al. Adv. Mater. 2004, 16 (21) 1890-1893
23. Mazzoleni et al. Bioelectromagnetics 1986, 7 (1) 95-9
24. Shin et al. ACS Nano 2013, 7 (3) 2369-80
25. Radisic et al. Proc. Natl. Acad. Sci. U.S.A. 2004, 101 (52) 18129-34
26. Beauchamp et al. Circ. Res. 2004, 95 (2) 170-8
27. Beauchamp et al. Circ. Res. 2012, 110 (11) 1445-53
28. You et al. Nano Lett. 2011, 11 (9) 3643-8
29. Dvir et al. Nature Nanotechnol. 2011, 6 (11) 720-5
30. Martinelli et al. ACS Nano 2013, 7 (7) 5746-5756
31. Zhou et al. Sci. Rep. 2014, 4, 3733
32. Rana et al. Toxicol. Sci. 2012, 130 (1) 117-31
33. Casey et al. Circulation 2000, 192 (25) 3124-9
34. Radisic et al. Biotechnol. Bioeng. 2006, 93 (2) 332-43
35. van den Heuvel et al. Mol. Cell. Cardiol. 2014, 67, 12-25
36. Rodriguez et al. Biophys. J. 2011, 101 (10) 2455-64
37. Bub et al. Am. J. Physiol. 2010, 298 (5) H1616-25
38. Yang et al. Circ. Res. 2014, 114 (3) 511-23

Example 2

Experimental Details

Electrically Conductive Silicon Nanowire Fabrication and Harvesting.

Single-crystalline SiNWs were synthesized using the nanocluster-catalyzed vapor-liquid-solid method described previously in a quartz tube connected to a gas manifold and vacuum pump and heated by a temperature controlled tube furnace.[1] Monodisperse gold nanoparticles (100 nm, Ted Pella) were dispersed on $SiO_2$/silicon substrates, which were placed within the central region of the quartz tube reactor. The SiNWs were synthesized at 470-485° C. using silane ($SiH_4$) as the silicon reactant source, $H_2$ as the carrier gas, and phosphine ($PH_3$, 1000 ppm in $H_2$) as the n-type dopants. In a typical synthesis of uniform n-type, 100 nm SiNWs, the flow rates of $SiH_4$, $PH_3$ and $H_2$ were 1-2, 2-4 and 60 standard cubic centimetres per minute, respectively, and the total pressure 40 torr. The nanowires were collected from the oxidized silicon substrates by sonication in isopropanol for 1 min followed by centrifugation to obtain SiNWs with an average dimension of 100 nm diameter and 10 μm length. The electrical conductivity of the SiNWs were measured by using four-probe transport measurement.

Cell Harvest and Culture.

Rat-neonatal cardiac cells were isolated from 2-day-old Sprague-Dawley rats by using the neonatal isolation kit (Worthington Biochemical Corporation, Lakewood, N.J.). Rat-neonatal cardiac cells and spheroids were cultured in Dulbecco's Modified Eagle Medium (DMEM, 4500 mg/L glucose) (Thermo Scientific, Pittsburgh, Pa.) containing 10% heat inactivated fetal bovine serum (HI FBS) (Life Technologies, Carlsbad, Calif.), 1% penicillin-streptomycin (Life Technologies, Carlsbad, Calif.), and 1% non-essential amino acids (Life Technologies, Carlsbad, Calif.). hiPSC-derived cardiomyocytes (iCell Cardiomyocytes, Cellular Dynamics International, Madison, Wis., USA) were cultured according to the manufacturer's protocol. Briefly, hiPSC-derived cardiomyocytes were plated on 0.1% gelatin coated 6-well plates in iCell Cardiomyocyte Plating Medium (Cellular Dynamics International) at a density of about $3 \times 10^5$ to $4.0 \times 10^5$ cells/well and incubated at 37° C. in 5% $CO_2$ for 4 days. Two days after plating, the plating medium was removed and replaced with 4 mL of iCell Cardiomyocytes Maintenance Medium (Cellular Dynamics International). After 4 days of monolayer pre-culture, cells were detached using trypLE Express (Gibco Life Technologies, Grand Island, N.Y.) and prepared for spheroid fabrication.

Spheroid Fabrication and Electrical Stimulation.

The agarose hydrogel molds were prepared using commercial master micro-molds from Microtissues, Inc (Providence, R.I.) as negative replicates to create non-adhesive agarose hydrogels molds containing 35 concave recesses with hemispheric bottoms (800 μm diameter, 800 μm deep) to facilitate the formation of tissue cell spheroids. 330 μL 1% sterile agarose solution was pipetted into the master micro-molds and was then carefully detached after gelation from the master mold and transferred into one well of a 24-well tissue culture plate. The schematic presentation of cell spheroids fabrication is shown in the FIG. 2C. A suspension of rat-neonatal cardiac cells and e-SiNWs in media was prepared at a 1:1 ratio (number of cells/number of SiNWs) with a concentration of $5.0 \times 10^6$ cells/mL. Similarly, hiPSC-derived cardiomyocytes were mixed with e-SiNWs in the Maintenance media at a 1:1 ratio (number of cells/number of SiNWs) with a concentration of $3.0 \times 10^6$ cells/mL. Approximately 75 μl of the cell/e-SiNW suspension (rat-neonatal cardiac cells, $5.0 \times 10^6$ cells/mL; hiPSC-CMs, $3.0 \times 10^6$ cells/mL) was pipetted into each agarose mold. After the cells had settled down into the recesses of the mold (10 min), additional media was added (5 mL) and exchanged every 2 days for the length of the experiment. After 4 days of spheroid culture, an electrical stimulation treatment (C-Pace unit, Ion Optix, Milton, Mass. 02186) was started for designated groups for 7 days (15 V, 1 Hz, 2 ms). For the long term culture experiment of hiPSC cardiac spheroids, the electrical stimulation treatment was performed for 21 days for the designated groups after the initial 4 days of spheroid culture.

Video and Image Analysis of Beating Spheroids.

Videos of 6 spheroids from each group were recorded starting after the initial 4 days of spheroid culture using Zen 2011 software (Zeiss, Göttingen, Germany) with capture rate of 14 frames per second. Then the videos were converted to a series of TIFF format pictures by Adobe Premiere (Adobe, San Jose, Calif.). Threshold edgedetecting in ImageJ software (National Institutes of Health) was used on high contrast spheroid pictures and graphed to realize contraction profiles, from which other quantifiers were calculated (i.e., fractional area change and beats per minute).

Histological and Immunofluorescent Analysis of Spheroids and Cells.

Freshly collected spheroids (~30-35) were placed onto a pre-labeled tissue base mold and the entire tissue block was covered with OCT. Immediately, the base mold containing spheroids was transferred into pre-cooled ethanol with dry ice to ensure that the spheroids were frozen completely. By using the cryotome, the frozen spheroids block were sectioned into 7 μm thickness layers onto glass slides for immunohistochemistry. The sections were fixed with pre-cooled acetone (−20° C.) for 10 min. The fixative was poured off and the acetone was allowed to evaporate from the sections for 20 min at room temperature. After washing (3 times at 5 min) in PBS with 0.1% Triton X-100 (PBST), 100 μl blocking buffer was added (10% goat serum in PBS) onto the sections of the slides and incubated in a humidified chamber at room temperature for 1 h. Sections were incubated with appropriately diluted primary antibody: alpha sarcomeric actinin (Abcam, Cambridge, UK), troponin I (Santa Cruz, Dallas, Tex.), connexin-43 (Sigma Aldrich, St. Louis, Mo.) and beta myosin heavy chain (Millipore, Billerica, Mass.) overnight at 4° C. After washing in PBST (3 times at 5 min), tissues were incubated with coordinate secondary antibodies diluted in PBST for 1 h at ambient temperature. After washing in PBST (3 times at 5 min), nuclei were counterstained with DAPI (Molecular Probes/Invitrogen, Eugene, Oreg.) diluted in PBST for 15 min at ambient temperature. Following the final wash procedure (PBST, 3 times at 5 min), glass cover slips were added to the slides using Fluoro-Gel (Electron Microscopy Sciences, Hatfield, Pa.). Finally, TCS SP5 AOBS laser scanning confocal microscope (Leica Microsystems, Inc., Exton, Pa.) was used to get fluorescent images. Fluorescent protein expression was calculated as the fluorescence area coverage divided by the number of nuclei.

TUNEL Staining for the Frozen Section of Spheroids.

In Situ Cell Death Detection Kit (Roche, Penzberg, Germany) was used to determine the viability of the cell in the frozen section of spheroids based on the protocol from website of Roche. Briefly, the frozen sections of spheroids were fixed with 4% paraformaldehyde in PBS for half hour at room temperature. Following washing in PBS for 30 minutes, samples were incubated in a permeabilization solution (0.1% Triton X-100 and 0.1% sodium citrate in PBS) for 2 minutes on ice. Then 50 ul of the TUNEL reaction mixture were added to samples and incubated in 37° C. for 1 hour. After washing in PBST (3 times at 5 min), nuclei were counterstained with DAPI (Molecular Probes/Invitrogen, Eugene, Oreg.) diluted in PBS for 15 min at ambient temperature. Following the final wash procedure (PBS, 3 times at 5 min), glass cover slips were added to the slides using Fluoro-Gel (Electron Microscopy Sciences, Hatfield, Pa.). Finally, TCS SP5 AOBS laser scanning confocal microscope (Leica Microsystems, Inc., Exton, Pa.) was used to get fluorescent images.

Western Blotting Analysis.

Following 7 days of cell culture with or without electrical stimulation, 30-35 spheroids from each rat-neonatal group were harvested from agarose molds. After centrifugation and washing by PBS once, 30 μl lysis buffer with 1% protease and phosphatase inhibitor cocktails (Pierce Biotechnology, Rockford, Ill.) was added into the vials containing pellet of spheroids. Thereafter, the mixture was homogenized by the FastPrep24 instrument (MP Biomedicals, Santa Ana, Calif.) to break down spheroids into single cells. After 30 minutes to lyse cells on ice, then tubes were centrifuged for 10 min at 10 000 g at 4° C. and the supernatant was collected as protein solution. After quantifying the protein concentration by using the bicinchoninic acid methods, the protein solution was mixed with 4×LDS sample loading buffer (Pierce Biotechnology) and boiled for 5 min. Protein samples of equal amount were separated in a 4%-12% Bis Tris NuPAGE gel (Life Technologies, Carlsbad, Calif.). Proteins were transferred to a PVDF membrane (Life Technologies) and blocked with 5% nonfat milk for one hour, followed by incubation with the following primary antibodies: alpha sarcomeric actinin (Abcam, Cambridge, UK), connexin-43 (Sigma Aldrich, St. Louis, Mo.), beta myosin heavy chain (Millipore, Billerica, Mass.), and GAPDH (Sigma Aldrich) overnight at 4° C. Blots were then probed with horseradish peroxidase-labeled secondary antibodies (Cell Signal, Danvers, Mass.) and visualized by an enhanced chemiluminescence detection kit (Amersham Pharmacia Biotech (GE Healthcare), Pittsburgh, Pa.). The intensity of each signal was analyzed by using ImageJ software.

Spheroid Spreading Assay.

Spheroids were seeded onto 0.1% gelatin-coated glass cover slips and incubated at 37° C., 5% $CO_2$, 20% $O_2$. Cell culture medium was changed every other day. After 12 days culture, the spheroids spread into a monolayer structure, which was suitable for immunofluorescent staining for high resolution, single cell, sarcomere structure analysis.

Single Cell Cardiomyocyte Analysis.

The average sarcomere length was defined as spacing between α-SA striations and was measured using black and white renderings of confocal α-SA-stained cardiomyocyte images, according to previous methods.[2] Using ImageJ, fluorescence profiles along lines passing perpendicular through 3 different striated regions of at least 9 cells, containing at least 6 consecutive sarcomere structures, were measured and divided by the number of sarcomeres (space between profile peaks). Z-line width, as previously explored,[3] was measured directly on α-SA-stained cardiomyocyte images in 12 cells with 15 measurements per cell. Z-line alignment was defined to establish a sensitive method for sarcomere alignment to reflect the enhanced contraction and synchronization. Calculations were made using an ImageJ plug-in, OrientationJ, which creates an orientation distribution output. The area under the curve at ±20° the peak orientation degree divided by the total area under the curve was established as the fraction Z-line alignment.

Calcium Transient Imaging of Cardiac Spheroids.

Fluo-4 Direct Calcium Assay Kits (Life Technologies, Carlsbad, Calif.) was used to label calcium ion in the whole spheroids based on the protocol from Life Technologies. Briefly, spheroids were seeded onto 0.1% gelatin-coated glass cover slips and incubated at 37° C., 5% $CO_2$, 20% $O_2$. Cell culture medium was changed every other day. After 4 days culture, the spheroids were rooted on the cover slips. Then cover slips with the spheroids were put into 12 wells plates with 2 ml calcium dye solution per well and incubated at 37° C., 5% $CO_2$, 20% O2 for 1 h. TCS SP5 AOBS laser scanning confocal microscope (Leica Microsystems, Inc., Exton, Pa.) was used to collect the videos of the calcium transient of whole spheroids with a capture rate of 14 frames per second. Finally, we used the software of LAS AF from Leica to conduct the quantification of videos collected by confocal.

qRT-PCR.

Total RNA was isolated according to the kit and protocol of an RNeasy Micro Kit (Qiagen, Vinlo, Netherlands) with the addition of the QIAShredder (Qiagen) during the homogenization step for spheroids. For each group, 20-35 spheroids were used for RNA isolation. At least 25 ng of total RNA for each group was subjected to cDNA synthesis using the Bio-Rad (Hercules, USA) iScript cDNA synthesis kit. qRT-PCR step was performed using "best coverage" validated Taqman primers (Life Technologies, Carlsbad, USA) in 10 μl reactions for the following genes:

CACNA1C, CACNA1G, GAPDH, GJA1, MYL2, ACTB. Data was normalized as the change in cycle threshold (Ct) to GAPDH and ACTB (dCt) and analyzed using, mRNA expression=2^(−(dCt)).

Transmission Electron Microscopy.

SiNWs were gently sonicated in isopropyl alcohol (IPA) and dispersed onto lacey carbon grids (Ted Pella Inc.). TEM imaging was conducted using a 300 kv FEI Tecnai G2 F30 Super Twin Transmission Electron Microscope. Spheroids were fixed with 2.5% glutaraldehyde, postfixed in PBS buffered 1% osmium tetroxide with 1.5% K+ ferricyanide, dehydrated in graded ethanol and acetonitrile, and embedded in PolyBed 812 (Polysciences). 70-nm thick spheroid sections were prepared by using a Leica UltraCut R and a diamond knife, stained with Hanaichi Pb citrate and uranyl acetate, and imagined using a JOEL 200 CX transmission electron microscope.

Statistics Analysis:

Differences between experimental groups were analyzed using a independent Student T-tests and one-way ANOVA followed by Tukey's post-hoc test. $P<0.05$ was considered significantly difference for all statistical tests.

MATERIAL AND METHODS REFERENCES

1. Wu et al. Nano Lett. 4, 433-436 (2004).
2. Fine. Am. J. Physiol. Cell Physiol. 305, C481-91 (2013).
3. Rodriguez et al. Biophys. J. 101, 2455-64 (2011).
4. Rezakhaniha et al. Biomech. Model. Mechanobiol. 11, 461-73 (2012).

Example 3

Drug Testing

To validate the effectiveness of the cardiac microtissues with semiconductor nanomaterials for high throughput drug cardiotoxicity screening, a known arrhythmic drug (quinidine) was used. After incubating the microtissues with 10 µM quinidine for 20 min, videos of microtissues were recorded and converted to a series of TIFF format pictures to calculate beating parameters. Beat period variation based on the standard deviation of beat period were calculated and used as a metric for detecting arrhythmia. As shown in FIG. 14, quinidine induced arrthymia was reproduced by using the microtissues. This demonstrated the potential of using the microtissues with semiconductor nanomaterials for high throughput drug cardiotoxicity screening.

Example 4

Injecting Nanowired hiPSC Cardiac Spheroids in Healthy Rat Hearts

Immuno-compromised Athymic rats are used as human cells are introduced into these rats, as these cells may cause immune rejection in normal rats. Young adult male Athymic rats (8-10 weeks old) are prepared for surgery, anesthetized, given analgesia, intubated, and a left thoracotomy is performed to expose the heart. The pericardium is opened and the left ventricle (LV) is visualized. After that, human cardiac microtissues with semiconductor nanomaterials are injected into the LV of the healthy rats at 3-4 sites (1.0 million cells per animal, n=10 rats). The sham-operated group is used as a positive control, and the rat hearts injected with PBS serve as another control as the injection surgery itself creates injuries in a healthy heart. Once the injections are completed, the thoracotomy incision is repaired and the animal is allowed to recover for either 7 or 28 days when it undergos heart harvest for histological analysis.

To conduct histological analysis, the harvested hearts are fixed, processed, embedded in OCT and sectioned. The frozen sections are stained for human nuclei specific antibody (Millipore) and α-SA antibodies to examine the engraftment of hiPSC-CMs. The size of cell engraftment is determined by examining 5 sections for each heart. Also, the sections are stained with N-cadherin and Cx-43 antibodies to examine the formation of adherens junctions and gap junctions between the engrafted hiPSC-CMs and host myocardium, respectively. In addition, they are stained with CD31 antibody to examine the perfusion of the host vessels into the hiPSC-CM grafts. To examine the proliferation of hiPSC-CMs after transplantation, the histological section are stained with Ki-67. These staining results allow for quantitative/qualitative examination of the effectiveness of the microtissues with semiconductor nanomaterials on cell engraftment and integration in healthy rat myocardium.

In addition to histological analysis, echocardiographic analysis is used to examine cardiac functions after cell transplantation. All rats undergo echocardiographic assessment for LV volumes and ejection fractions before and after cell injection; some 28-day time point rats may have weekly measurements.

Injecting Nanowired hiPSC Cardiac Spheroids in Infarcted Rat Hearts

Immuno-compromised Athymic rats are used to create models of myocardial infarction to examine the efficacy of nanowired hiPSC cardiac spheroids. Young adult male Athymic rats (8-10 weeks old) are prepared for surgery, anesthetized, given analgesia, intubated, and a left thoracotomy is performed to expose the heart. The pericardium is opened and the left ventricle is visualized. A 7-0 prolene suture is placed around the left anterior descending artery (LAD) just below the first major branch and the artery is tied off. The incision site is repaired and the animals recover for 4 days. After that, human cardiac microtissues with semiconductor nanomaterials are injected to the region surrounding the infarcted area at 3-4 sites (1.0 million cells per animal, n=10 rats). Myocardial infarcted rats without the cell injection are used as negative control, and sham-operated group is used as positive control. Once the injections have been completed, the thoracotomy incision is repaired and the animal is allowed to recover for either 7 or 28 days when it undergos heart harvest for histological analysis.

The frozen sections are stained with Masson's Trichrome (collagen) staining and immunofluorescent staining of α-SA (cardiomyocyte marker) and vimentin (Vm; noncardiomyocyte marker) to identify the infarction region. The graft size is determined by using human nuclei specific antibody (Millipore) and α-SA antibody. The integration between transplanted hiPSC-CMs and host myocardium is examined by staining with N-cadherin and Cx-43 antibodies. In addition, the sections are stained with CD31 antibody to examine the perfusion of the host vessels into the hiPSC-CM grafts. They are also stained with Ki-67 to examine the proliferation of hiPSC-CMs after transplantation. These staining results allow for quantitative/qualitative examination of the effectiveness of the microtissues with semiconductor nanomaterials on cell engraftment and integration in the infarcted rat hearts.

In addition to histological analysis, echocardiographic analysis is used to examine the functional improvement after cell transplantation. All rats undergo echocardiographic assessment for LV volumes and ejection fractions before and after myocardial infarction/cell injection; some 28-day time point rats may have weekly measurements.

Injecting Nanowired Neonatal Cardiac Spheroids in Healthy Rat Hearts

Immuno-compromised Athymic rats are used to introduce cardiac cells from one rat into another rat, which may cause the immune rejection in normal rats. Young adult male Athymic rats (8-10 weeks old) are prepared for surgery, anesthetized, given analgesia, intubated, and a left thoracotomy is performed to expose the heart. The pericardium is opened and the left ventricle (LV) is visualized. After that, cell tracker/virus labeled rat neonatal cardiac microtissues with semiconductor nanomaterials are injected to the LV of the healthy rats at 3-4 sites (1.0 million cells per animal, n=10 rats). The sham-operated group is used as positive control, and the rat hearts injected with PBS serve as another control as the injection surgery itself creates injuries in a healthy heart. Once the injections have been completed, the thoracotomy incision is repaired and the animal is allowed to recover for either 7 or 28 days when it undergoes heart harvest for histological analysis.

To conduct histological analysis, the harvested hearts are fixed, processed, embedded in OCT and sectioned. The cell engraftment is examined by using cell tracker/virus label. Also, the sections are stained with N-cadherin and Cx-43 antibodies to examine the formation of adherens junctions and gap junctions between the engrafted cardiac cells and host myocardium, respectively. In addition, they are stained with CD31 antibody to examine the perfusion of the host vessels into the grafts. To examine the proliferation of neonatal cardiac cells after transplantation, the histological section are stained with Ki-67. These staining results allow for the effectiveness of the microtissues with semiconductor nanomaterials on cell engraftment and integration in healthy rat myocardium to be quantitatively/qualitatively examined.

In addition to histological analysis, echocardiographic analysis is used to examine cardiac functions after cell transplantation. All rats undergo echocardiographic assessment for LV volumes and ejection fractions before and after cell injection; some 28-day time point rats may have weekly measurements.

Injecting Nanowired Rat Neonatal Cardiac Spheroids in Infarcted Rat Hearts

Immuno-compromised Athymic rats are used to create models of myocardial infarction to examine the efficacy of nanowired rat neonatal cardiac spheroids. Young adult male Athymic rats (8-10 weeks old) are prepared for surgery, anesthetized, given analgesia, intubated, and a left thoracotomy is performed to expose the heart. The pericardium is opened and the left ventricle is visualized. A 7-0 prolene suture is placed around the left anterior descending (LAD) artery just below the first major branch and the artery is tied off. The incision site is repaired and the animals recovers for 4 days. After that, cell tracker/virus labeled rat neonatal cardiac microtissues with semiconductor nanomaterials are injected to the region surrounding the infarcted area at 3~4 sites (1.0 million cells per animal, n=10 rats). Myocardial infarcted rats without the cell injection are used as negative control, and sham-operated group is used as positive control. Once the injections have been completed, the thoracotomy incision is repaired and the animal is allowed to recover for either 7 or 28 days when it undergos heart harvest for histological analysis.

The frozen sections are stained with Masson's Trichrome (collagen) staining and immunofluorescent staining of α-SA (cardiomyocyte marker) and vimentin (Vm; noncardiomyocyte marker) to identify the infarction region. The graft size is determined by using cell tracker and/or virus labeling. The integration between transplanted cells and host myocardium is examined by staining with N-cadherin and Cx-43 antibodies. In addition, the sections are stained with CD31 antibody to examine the perfusion of the host vessels into the grafts. They are also stained with Ki-67 to examine the proliferation of the transplanted rat neonatal cardiac cells after transplantation. These staining results allow for the effectiveness of the microtissues with semiconductor nanomaterials on cell engraftment and integration in the infarcted rat hearts to be quantitatively/qualitatively examined.

In addition to histological analysis, echocardiographic analysis is used to examine the functional improvement after cell transplantation. All rats undergo echocardiographic assessment for LV volumes and ejection fractions before and after myocardial infarction/cell injection; some 28-day time point rats may have weekly measurements.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A tissue comprising cardiac cells, a semiconductor nanomaterial, and an electrically conductive microenvironment,
   wherein the electrically conductive microenvironment consists of an electrically conductive network within the tissue, wherein the electrically conductive network comprises the cardiac cells and the semiconductor nanomaterial;
   wherein the semiconductor nanomaterial is incorporated within the tissue and the semiconductor nanomaterial is present in the tissue in an amount of about 0.00001% to about 1% by weight of the semiconductor nanomaterial per volume of the tissue;
   wherein the tissue is scaffold-free and is a three-dimensional tissue; and
   wherein the tissue is a spheroid or an aggregate.

2. The tissue of claim 1, wherein the cardiac cells comprise cardiomyocytes and/or cardiac fibroblasts.

3. The tissue of claim 1, wherein the semiconductor nanomaterial is an n-type or p-type semiconductor nanomaterial.

4. The tissue of claim 1, wherein the semiconductor nanomaterial is biocompatible and/or biodegradable.

5. The tissue of claim 1, wherein the semiconductor nanomaterial has a diameter in a range of about 10 nm to about 200 nm.

6. The tissue of claim 1, wherein the semiconductor nanomaterial has a length of about 1 μm to about 20 μm.

7. The tissue of claim 1, wherein the semiconductor nanomaterial comprises a silicon nanomaterial.

8. The tissue of claim 7, wherein the silicon nanomaterial is a silicon nanowire and/or nanotube.

9. The tissue of claim 7, wherein the silicon nanomaterial has a silicon:phosphorous ratio in a range of about 10:1 to about 10000:1 and/or a silicon:borane ratio in a range of about 10:1 to about 10000:1.

10. The tissue of claim 1, wherein the semiconductor nanomaterial has a conductivity in a range of about 0.001 μS/μm to about 2000 μS/μm.

11. The tissue of claim 1, further comprising vascular cells.

12. The tissue of claim 1, wherein the semiconductor nanomaterial is present in the tissue in an amount of about 0.00001% to about 0.01% by weight of the semiconductor nanomaterial per volume of the tissue, and
wherein the semiconductor nanomaterial has a diameter of about 10 nm to about 200 nm and a length of about 1 μm to about 20 μm.

13. The tissue of claim 1, wherein the tissue is prepared from a cell culture having a ratio of cardiac cells to semiconductor nanomaterial in a range of about 0.5:1 to about 100:1 (number of cells:number of semiconductor nanomaterials).

14. The tissue of claim 1, wherein the electrically conductive network provides synchronized electrical signal propagation within the tissue.

15. The tissue of claim 1, wherein the tissue is a functional cardiac microtissue.

16. The tissue of claim 1, wherein the tissue is in the form of a spheroid.

17. A method of screening a compound or composition, the method comprising:
introducing and/or contacting the compound or composition to a tissue of claim 1.

18. The method of claim 17, further comprising detecting a response to the compound or composition.

19. A method of repairing cardiac tissue in a subject, the method comprising implanting a tissue of claim 1 into the cardiac tissue of the subject.

* * * * *

UNITED STATES PATENT AND TRADEMARK OFFICE
CERTIFICATE OF CORRECTION

Page 1 of 1

PATENT NO. : 10,988,735 B2
APPLICATION NO. : 15/543701
DATED : April 27, 2021
INVENTOR(S) : Mei et al.

It is certified that error appears in the above-identified patent and that said Letters Patent is hereby corrected as shown below:

On the Title Page

Item (54) Title: Please correct "CARDIAC TISSUES" to read -- TISSUES --

In the Specification

Column 1, Line 1: Please correct "CARDIAC TISSUES" to read -- TISSUES --

Column 3, Line 43: Please correct "φ-MHC" to read -- β-MHC --

Column 14, Line 63: Please correct "P-MHC" to read -- β-MHC --

Column 20, Line 37: Please correct "output." to read -- output.⁴ --

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*